United States Patent
Sippel et al.

(12)

(10) Patent No.: US 6,432,531 B1
(45) Date of Patent: Aug. 13, 2002

(54) SYNTHESIS OF ALUMINA ACETATE MONOHYDRATE SALT SOL FIBERS AND USES THEREOF

(76) Inventors: Roy J. Sippel, 153 Pierson Rd., Woodstown, NJ (US) 08098; Eugene A. Pasek, 115 Maple Pl., Fayetteville, GA (US) 30215; Ke Feng, 1205 Greenmont Hills Dr., Vienna, WV (US) 26105

( * ) Notice: Subject to any disclaimer, the term of this patent is extended or adjusted under 35 U.S.C. 154(b) by 0 days.

(21) Appl. No.: 09/861,312

(22) Filed: May 18, 2001

Related U.S. Application Data

(63) Continuation-in-part of application No. 08/842,047, filed on Apr. 23, 1997, now abandoned, which is a continuation-in-part of application No. 08/639,960, filed on Apr. 29, 1996, now abandoned.

(51) Int. Cl.[7] ............................ B32B 19/00; B01J 20/04
(52) U.S. Cl. ...................... 428/357; 428/364; 428/367; 556/170; 562/607; 502/415
(58) Field of Search ................................ 428/357, 364, 428/367; 556/170; 562/548, 607; 502/415, 355

(56) References Cited

U.S. PATENT DOCUMENTS 3,207,578 A * 9/1965 Brown et al. .................. 23/143
3,790,495 A * 2/1974 Podschus ................ 252/313 R

* cited by examiner

Primary Examiner—Cynthia H. Kelly
Assistant Examiner—J. M. Gray
(74) Attorney, Agent, or Firm—Herbert M. Hanegan; Dale Lischer; Eric J. Hanson

(57) ABSTRACT

A cationic fibrous acetate salt of boehmite alumina produced by providing a slurry of water and basic aluminum acetate, stirring the slurry to ensure substantially complete mixing thereof, reacting the slurry in a vessel for a time, temperature, and stirring rate sufficient to produce a fibrous cationic acetate salt of boehmite alumina having a zeta potential of greater than about 25 and a weight ratio of aluminum to acetate of less than about 4.

34 Claims, 11 Drawing Sheets

US 6,432,531 B1

SYNTHESIS OF ALUMINA ACETATE MONOHYDRATE SALT SOL FIBERS AND USES THEREOF

CROSS REFERENCE TO RELATED APPLICATION

This is a continuation-in-part of application Ser. No. 08/842,047, filed Apr. 23, 1997, now abandoned which was a continuation-in-part of application Ser. No. 08/639,960, filed Apr. 29, 1996 abandoned.

FIELD OF THE INVENTION

The present invention relates to a novel composition of matter, and its method of production. Also disclosed is a process for dyeing cotton and other similar fabrics and for removing waste from waste streams including waste streams containing dyes that are not completely trapped by or attached to the fibers in the dyeing process. Although the dyeing and dye removal process will be explained relative to direct dyes, it should be understood that the processes are equally usable with any other dyes, i.e.,—direct, acid, sulfur or reactive dyes, any dye that has a negative charge or partial negative charge.

Dyeing is accomplished by placing a solution containing a dye in contact with fibers or fabric composed of many fibers. The dye is entrapped within or attached to the latices of the entwined fibers. The fibers or fabric are then washed to remove the dye that is not fixed, i.e., not fully attached or trapped. In the past the dye that was not trapped or attached was discharged as waste effluent in addition to the spent dye bath, which has a higher concentration than the washing effluent. Not only was a considerable quantity of valuable dye lost, but the effluent needed to be treated before being discharged into streams. The word dye as used herein includes dyestuff and the like formulations or combinations of dyes and carriers, fillers, and the like.

BACKGROUND OF THE INVENTION

The present invention relates to a method of purifying a waste stream or effluent. The invention also relates to a composition of matter for use in this method. More particularly the present invention relates to dyeing and to municipal and dye waste stream purification by flocculation and/or precipitation.

In terms of application, the invention relates to a method for purification of contaminated municipal and dye waste streams which can remove a substantial amount of the contaminants therefrom.

SUMMARY OF THE INVENTION

It is an object of the present invention to provide a composition of matter adapted to be used for dyeing fabrics and for use in dye waste stream treatment processes which composition is capable of dyeing fabrics and also removing a substantial amount of dye from the dye waste stream thereby reducing the treatment cost.

Another object of the invention to provide an improved dye waste stream treatment latex method for the clarification of dye waste streams with increased efficiency, at reduced cost and in a simpler manner than has been possible heretofore.

Still another object of the invention is to provide an improved method of removing contaminants from a municipal waste stream which will increase the degree of decontamination for a given treatment cost over that which is attainable by prior methods.

The foregoing objects and others which will be apparent subsequently are obtained through the present invention by application of a flocculation or precipitation agent to the dye waste stream.

Accordingly, an important feature of the present invention, the composition of matter, is fibrous acetate salt of boehmite alumina which precipitates, associates with and/or flocculates the anionic dyes.

BRIEF DESCRIPTION OF THE DRAWINGS

The following includes a detailed description of the invention, which should be considered in conjunction with the attached figures, wherein.

DESCRIPTION OF THE PREFERRED EMBODIMENTS

Figure 1:
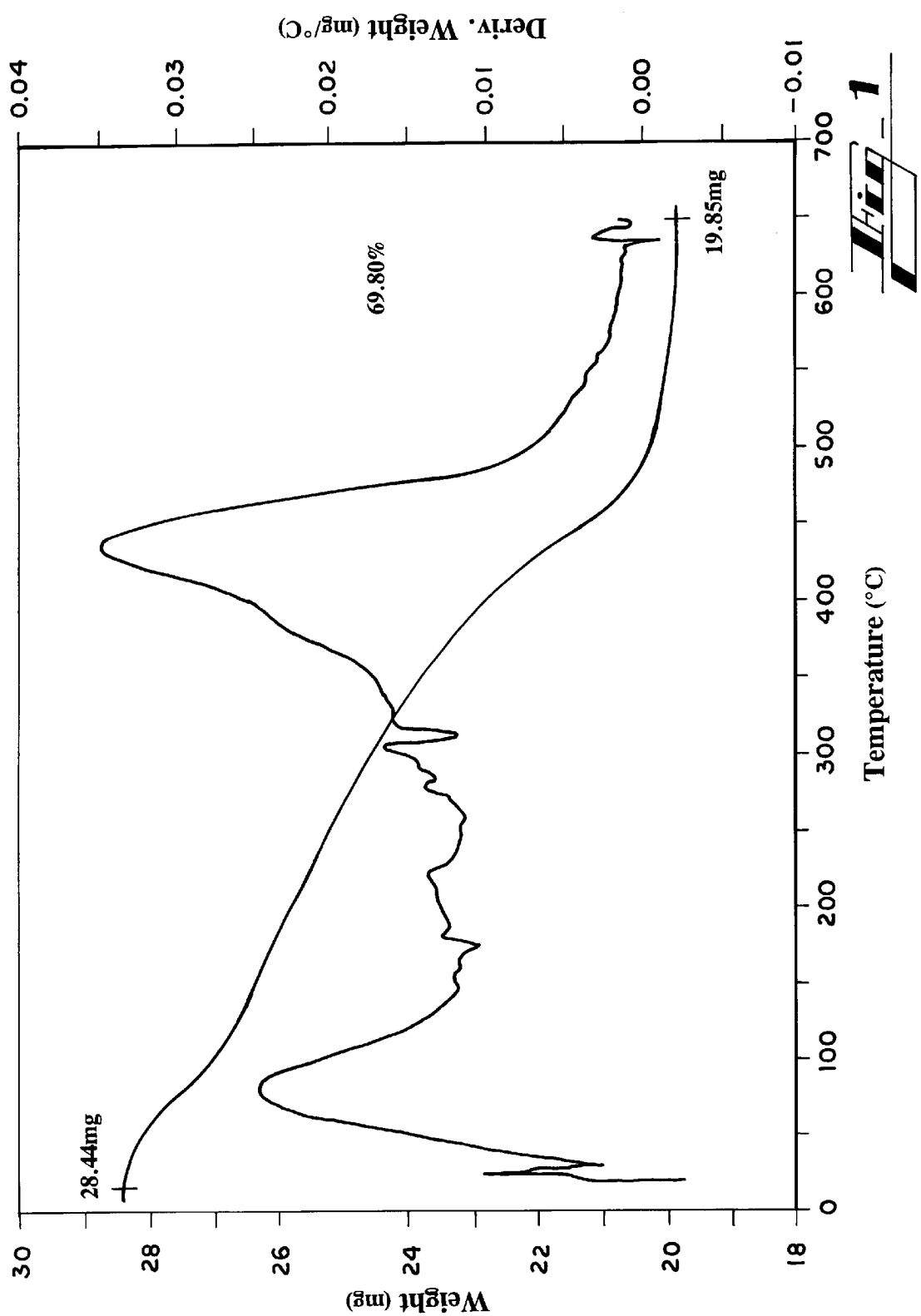
FIG. 1 shows the thermal residual weight of a sample prepared at 140° C. when heated to 650° C.

The present inventive process aids in dyeing fabrics, removes contaminants from municipal waste streams and removes dye which was untrapped by or unattached to fibers from a dye bath waste stream and optionally may recycle the removed dye to the dyeing process. In one embodiment, fibrous acetate salt of boehmite alumina is added to the discharge waste stream from the dyeing process.

The cationic fibrous acetate salt of boehmite alumina of the present invention is produced by providing a slurry of water and basic aluminum acetate, stirring the slurry to ensure substantially complete mixing thereof, reacting the slurry in a vessel for a time, temperature, and stirring rate sufficient to produce a fibrous cationic acetate salt of boehmite alumina having a zeta potential of greater than about 25 and a weight ratio of aluminum to acetate of less than about 4. Advantageously the fibrous salt of the present invention has an acetate content of from more than about 13 to about 45 weight percent, preferably from about 20 to about 40 weight percent. Advantageously, the fibrous acetate has at least about 40% more active/reactive sites than commercially available colloidal alumina. Preferably the fibrous acetate has a surface area to total volume ratio of at least about 50%. Advantageously the slurry of the present invention contains on the basis of $Al_2O_3$ from about 0.5 weight % to about 30 weight % $Al_2O_3$, preferably from about 0.5 weight % to about 15 weight % $Al_2O_3$.

Advantageously the slurry is stirred for from less than about 1 minute to about 60 minutes prior to initiating the reaction, preferably from about 5 minutes to about 30 minutes.

Advantageously the slurry is reacted at a temperature of from about 100° C. to less than 140° C., preferably from about 100° C. to about 130° C. and most preferably from about 120° C. to about 130° C.

Advantageously the slurry is reacted for a time of from less than about 1 second to about 240 minutes. Depending on the type of final product desired, the slurry can be reacted for a time of from about 10 minutes to about 120 minutes. Advantageously, the slurry is reacted at a temperature of about 130° C. for about 120 minutes for one type of final product. Another type of product is produced where the slurry is reacted at a temperature of about 135° C. for less than about 5 seconds, wherein the slurry temperature increase is halted and cooling is started when the slurry temperature reaches 135° C. Advantageously the slurry is stirred during the reaction at a rate of from about 50 to about 800 rpm After completion of the reaction, the reacted slurry is advantageously cooled to a temperature of from about 20° C. to about 100° C.

The present invention encompasses a process for the dyeing of fibers with a dye selected from the group consisting of direct, reactive, sulfur and acid dyes whereby in the dye process undyed fibers are passed through a dye bath, containing dye which is associated with or attached to a cationic fibrous acetate salt of boehmite alumina having a zeta potential of greater than about 25, a weight ratio of aluminum to acetate of less than about 4, and where the fibers to be dyed remove the dye from the fibrous acetate salt of boehmite alumina upon contact therewith; wherein the cationic fibrous acetate salt of boehmite alumina has been formed by providing a slurry of water and basic aluminum acetate, stirring the slurry to ensure substantially complete mixing thereof, and reacting the slurry in a vessel for a time, temperature, and stirring rate sufficient to produce cationic fibrous acetate salt of boehmite alumina.

Another embodiment of the present invention is a process of treating a dye waste stream comprising the steps of introducing into the stream at least one agent which forms a flocculant or precipitant with the dye, said agent consisting of a cationic fibrous acetate salt of boehmite alumina, the balance being predominantly a component selected from the group which consists of inorganic salts, coagulants, organic flocculants, polymeric flocculants, and combinations thereof, said agent being formed by providing a slurry of water and basic aluminum acetate, stirring the slurry to ensure substantially complete mixing thereof, and reacting the slurry in a vessel for a time, temperature, and stirring rate sufficient to produce a cationic fibrous acetate salt of boehmite alumina having a zeta potential of greater than about 25 and a weight ratio of aluminum to acetate of less than about 4; forming a precipitate or flocculant of the dye and agent; and separating said resulting flocculant or precipitant from the stream. In this process the agent advantageously has an ionic charge opposite to that of the dye contained in the dye waste stream whereby the dye is attached to the agent by ionic substitution. Preferably the agent has a positive ionic charge and the dye has a negative ionic charge. Advantageously the process includes the step of adjusting the pH of the waste stream and fibrous acetate suspension to between about 2 and about 8. Preferably, the precipitate or flocculant is removed by flotation separation and filtered and includes the step of separating the dye from the precipitate or flocculant and the step of regenerating the dye from the precipitate or flocculant. Such regeneration may be by contacting the precipitant or flocculant with a negatively charged group. Advantageously the negatively charged group of this process is selected from OH– and $CO_3^{-2}$. Optionally the separated or regenerated dye is used in the dyeing process.

A further embodiment of the present invention is a process for removing contaminants from a municipal waste treatment stream which comprises adding a cationic fibrous acetate salt of boehmite alumina to the waste stream; forming a precipitate or flocculant of the contaminants and the fibrous acetate salt; and separating the precipitate or flocculant from the waste stream; wherein the cationic fibrous acetate salt of boehmite alumina has been formed by providing a slurry of water and basic aluminum acetate, stirring the slurry to ensure substantially complete mixing thereof, and reacting the slurry in a vessel for a time, temperature, and stirring rate sufficient to produce a cationic fibrous acetate salt of boehmite alumina having a zeta potential of greater than about 25 and a weight ratio of aluminum to acetate of less than about 4.

Prior to the present invention the dye waste stream was simply treated and discharged as effluent. Using the present process one can remove the dye, optionally regenerate the dye, and reuse or discharge the substantially dye-free stream.

Advantageously, the ionic charge of the fibrous acetate salt of boehmite alumina is opposite to that of the dye. Preferably the fibrous acetate has a positive charge and the dye has a negative charge. Since the dye is negatively charged, it is attracted to and attaches to the positively charged fibrous acetate. The differences in the charges result in a high degree of reactivity or attachment between the dye and the fibrous acetate. Although the adsorption of the dye onto the surface of the fibrous acetate accounts for a portion of the unexpectedly superior results of the fibers of the present invention, it is believed that the reactivity resulting from the difference in charge between the fibrous acetate and the dye is in a large part responsible for the unexpected results evident in the removal of a substantial portion of the dye from the waste stream.

One aspect of the present invention is that the surface area to volume ratio of the fibrous acetate can be about 50% or greater, i.e., the ratio of surface area to total volume can be about 50% or more. The fibrous acetate may be produced in accordance with the present invention from basic aluminum acetate.

Basic aluminum acetate may be prepared from alumina trihydrate and acetic acid. With elevated temperature and pressure, basic aluminum acetate is then hydrolyzed to produce alumina monohydrate which polymerizes to form fibers. The overall process can be expressed chemically as:

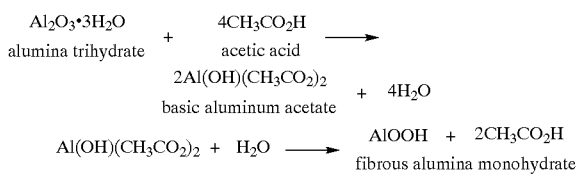

The equation shows the formation of boehmite; however, the product of this invention is actually a boehmite acetate salt. Basic aluminum acetate can also be formulated as $Al_2O(CH_3CO_2)_4 \cdot H_2O$. The sol product is composed of alumina monohydrate fibers, acetic acid and water.

The reaction conditions, temperature, solids concentration, pH and stirring rate dominate the dimensional characteristics of the fibers. An experimental reaction design was performed to establish the relationship between the reaction condition and physical state of the product. Upon examination fibers with unexpected dimensional characteristics were found to have been generated from the experiments. Some fibers were short and very wide, for example, and others were flexible and hair-like. Such fibers with novel shapes have not been reported in literature.

Solids concentration and temperature are parameters that directly impact the size and dimensions of fibers and bundles. Bundles are large aggregations of individual fibers and are generated at specific reaction conditions.

It is surprising that, when an alumina acetate monohydrate salt fiber of the type described is introduced in a form, such as cakes, chips, particles, plates or shaped bodies, and placed in contact with the dye waste stream to be treated, flocculation or precipitation of the dyes take place therein without contamination of the stream with other ionic species.

Advantageously, the pH of the waste stream is adjusted to between about 2 and about 8 by the addition of mineral acids or organic acids which aids in the precipitation or flocculation of alumina acetate monohydrate salt fibers and dye. The dye (excluding reactive dyes) may be regenerated or separated and recycled to be used in the dyeing process. Preferred results are obtained when the waste stream has a pH of between about 3 and about 5. A sufficient quantity of fibrous acetate can be added to the dye waste stream in any convenient manner.

One method of separating the precipitate or flocculant is by the use of a flotation separator. Flotation of the particles may be achieved by supersaturation with air under pressure. The pressure is then released and the air in the suspension lifts the particles to the surface. The floating particles are then removed by a mechanical skimmer and the waste decolorized effluent discharged. The particles can then be recycled and used in the dyeing process by any convenient means. The concentration of the particles can also be increased by filtration through a filter. A large percentage of the alumina monohydrate fibers used in the precipitation or flocculation process can be easily recovered.

While flotation separation is a preferred method of separation, the removed dye can be separated by other methods such as high pressure filtration. However, high pressure filtration requires more energy than the flotation separation.

An important aspect of the present invention is the possibility that the dye in certain instances can be regenerated, returned to the dyeing process and reused. As discussed above, it is believed that solubility based on the differences in charge between the fibrous acetate and the dye is in a large part responsible for the unexpected results of the present invention. The dye may be regenerated by substituting a negatively charged group for the negatively charged dye, thereby releasing the dye from the fibrous acetate. Advantageously such negatively charged group is an $OH^-$, $CO_3^{-2}$, or the like alkaline group. Preferably the precipitate or flocculant is filtered and a negatively charged group is used to contact the filter cake containing the alumina acetate monohydrate salt fibers and dye, thereby substituting the negatively charged group for the dye and releasing the dye to be reused.

Thus, the inventive process removes dye from waste streams containing dyes. This process may be batch or may be operated on a continuous basis.

In commercial processes the dyeing of fabric can be an environmental hazard. Commercial processes require heating of the dye bath up to 90° C. and adding, up to 10% sodium salt, as either chloride, or sulfate for proper coloration. Application of the fibrous alumina acetate before dyeing the fabric (pre-treatment) can reduce or eliminate the need for heating the dye solution and the need for salt addition.

In the present day textile coloration industry the efficiency of the technology allows about 10–50% of the dyes to go into the spent dye effluent. While most of the dyes are not toxic, these colored substances are classified as pollutants which constitute a very serious environmental problem facing the textile industry.

The present industry method used to manage the spent dye-bath is dilution. The dye solution is diluted to a very large volume so the concentration of dye is lower than the release regulation. This method is practical and economical but would be phased out if the total volume of release is regulated. Some other technologies being studied for removal of color from effluent include: 1) oxidation by ozone or other oxidation agents; 2) adsorption onto activated carbon; 3) filtration and electrolysis; 4) chlorination in basic solution; and 5) coagulation and/or flocculation. Among these methods, the coagulation and/or flocculation is considered by experts in the field to be the best, particularly in view of the costs and efficacies of the processes.

The highly cationic boehmite alumina acetate fibrous solution of the present invention is preferably generated in a pressure vessel (Parr reactor Model 4522M), and the process advantageously is summarized in four stages:

preparation of basic aluminum acetate (BAA) slurry rapid heating to a mild temperature minimal reaction time at the designed temperature cool down and discharge Preparation of BAA Slurry A slurry was made with deionized water and in-house prepared basic aluminum acetate (BAA). 1357 g of deionized water was added to 143 g of a BAA, and the slurry stirred via a magnetic stirring bar for 10 minutes. The stirred slurry was then placed in the reactor quickly to prevent any settling. The reactor was closed and the agitation was set at 200–400 RPM. The heating switch on the control panel was turned to the high position.

Rapid Heating to a Mild Temperature

The heating rate varied from 4° C./minute at the beginning to 5° C./minute toward the desired temperature. Since sufficient temperature is needed to complete the hydrolysis of the BAA, a mild reaction temperature range, 100–130° C., is desired for this process.

Minimal Reaction Time at the Desired Temperature

Once the temperature reached the desired temperature, e.g. 135° C., the heating was stopped by turning the heating switch on the control panel to the off position. Ice water was immediately pumped into the cooling coil inside the reactor. The solution was thus at the reaction temperature for less than one minute.

Cool Down and Discharge

While the cold water was pumped through the cooling coil, stirring was continued. When the contents were cooled to 50° C., the pumping of cold water was stopped and the solution discharged. The cool down process took about 10 minutes.

Such reaction conditions, mild reaction temperature with minimal reaction time, are desired to complete the hydrolysis of BAA and restrict the growth of the boehmite alumina acetate fibers. Small fibers afford higher specific surface area as well as the desired charge density.

While the above preparation used a pressure vessel, any type of equipment that permits rapid heating and cooling of a slurry could be used for the preparation of this type of material.

The alumina monohydrate sol so produced, dried at 350° C., is comprised of a unique boehmite alumina acetate salt. The high degree of cationic character of this salt is responsible for its reaction/adsorption with textile dye stuffs and waste water remediation.

The characterization of the alumina acetate salt fibers was done by a variety of analytical techniques. Among these were scanning electron microscopy (SEM) and transmission electron microscopy (TEM); thermogravimetric methods and acid titration of acetic acid content in the sols; particle size analyses; and zeta potential. In addition, textile dye adsorption maxima have provided further insight into the nature of the alumina sols.

Thus, in an effort to better characterize the alumina acetate salt (AMS) fibers and establish that these are different from simple, well known alumina monohydrate, boehmite, several additional analytical techniques were investigated. These included elemental analysis, thermogravimetric analyses (TGA), X-ray diffraction and infrared spectroscopy.

A. 3.0 weight percent as $Al_2O_3$ sol was generated in the 2-liter Parr reactor at 130° C. for 2 hours. These reaction conditions produced sols comprised of short thin fibers. A second 3.0 weight percent as $Al_2O_3$ sol was generated in the same reactor at 135° C. with zero holding time at this temperature, e.g. the mixture was heated only to temperature. This latter material contained only very small fibers (<145 mn in length (TEM)).

Samples of the two sols were air dried at ambient temperatures and then elemental analysis was performed for aluminum, carbon and hydrogen.

TGA was run on the air dried sample using a DuPont 9900 thermogravimetric cell. Two different techniques were used to examine this sample. First, the sample was dried at 80° C. for 15 minutes prior to ramping the temperature (20° per minute) to 650° C. and secondly by ramping to 650° C. without any drying period. Additional samples of the air dried sol were heated at 80° C. for 17 hours and another at 350° C. for 2 hours.

Similarly, an air dried sample was also examined by TGA methods. Two samples were examined: one where the temperature ramping was at 20° C. per minute and the other at 2° C. per minute.

X-ray diffraction was run on these dried sols.

Infrared spectra of sol air dried: 1) at ambient temperature, 2) at 80° C. for 17 hours, and 3) at 350° C. for 2 hours were obtained. The solids were prepared as potassiumbromide wafers.

Elemental Anales

1. Sample Prepared at 130° C./2 hrs

The elemental analyses of the air dried sample of a 3 weight percent sol prepared at 130° C./2 hours gave the following weight percentages: 4.92 carbon, 3.08 hydrogen and 32.32 aluminum. The difference between this sum (40.32%) is considered to be oxygen: 59.68 percent. Assuming the carbon is only associated with acetate ion, the acetate content is calculated to be 12.10 percent. The percent carbon, hydrogen and oxygen in the 12.10 percent acetate is thus:

| ELEMENT | WEIGHT PERCENT |
|---|---|
| Carbon | 4.92 |
| Hydrogen | 0.62 |
| Oxygen | 6.56 |
| Total (Acetate) | 12.10 |

The remaining percent hydrogen, oxygen and aluminum are shown below, along with the moles, normalized moles and charge balance for acetate and these elements:

| ELEMENT/ ION | WEIGHT PERCENT | MOLES | NORMALIZED MOLES | CHARGE BALANCE |
|---|---|---|---|---|
| Acetate | 12.10 | 0.205 | 0.171 | −0.171 |
| Aluminum | 32.32 | 1.20 | 1.00 | +3.00 |
| Hydrogen | 2.46 | 2.44 | 2.03 | +2.03 |
| Oxygen | 53.12 | 3.32 | 2.55 | −5.10 |

Although the charge is not in perfect agreement (+5.03 versus −5.27), this is assumed to be due to slight errors in the elemental analyses. If it is assumed that two aluminum atoms exist in this material, e.g. that it is an alumina, the empirical formula (molecular weight 155.03 gram/mole) for the material can be written:

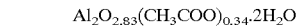

$Al_2O_{2.83}(CH_3COO)_{0.34} \cdot 2H_2O$

2. Sample Prepared at 135° C./0 hrs.

The elemental analyses for this air dried sol was found to be the following weight percent: 8.79 carbon, 3.70 hydrogen and 30.60 aluminum. The remainder is assumed to be oxygen. If, as above, all the carbon is assumed to be as acetate ion the following percentages for the elements and total acetate are calculated:

| ELEMENT | WEIGHT PERCENT |
|---|---|
| Carbon | 8.79 |
| Hydrogen | 1.10 |
| Oxygen | 11.72 |
| Total (Acetate) | 21.61 |

Thus, this sol contains considerably more acetate than the sol generated at 130° C. for 2 hours. The remaining percentages for the elements, along with this calculated acetate, are given below:

| ELEMENT/ ION | WEIGHT PERCENT | MOLES | NORMALIZED MOLES | CHARGE BALANCE |
|---|---|---|---|---|
| Acetate | 21.61 | 0.366 | 0.324 | −0.324 |
| Aluminum | 30.60 | 1.13 | 1.00 | +3.00 |
| Hydrogen | 2.60 | 2.58 | 2.28 | +2.28 |
| Oxygen | 45.19 | 2.82 | 2.50 | −5.00 |

The charge balance appears to be quite good for the analyses of this material/compound, e.g. +5.28 versus a −5.32. If as above the compound is assumed to contain two aluminum atoms in its empirical formula, the compound can be written as:

$$Al_2O_{2.68}(CH_3COO)_{0.64} \cdot 2.25H_2O$$

Dye Adsorption

1. Sample Prepared at 130° C./2 hrs.

The dye adsorption of C.I. Direct Red 80 for this sol freshly generated at 130° C. for 2 hours gives 2800 mg of dye per gram of $Al_2O_3$. However, values of nearly 5000 mg per gram of alumina are observed for an "aged" sol retain sample. If it is assumed that an adsorption site exists for every acetate molecule, the number of sites are calculated as 0.0033 moles per gram of alumina, $Al_2O_3$. Based on a molecular weight of 1417 gram/mole for Direct Red 80 and one dye molecule per site is adsorbed, the theoretical amount of dye which can be adsorbed is calculated to be 4700 mg per gram alumina. The empirical formula is thus consistent with the adsorption of dye.

2. Sample Prepared at 135° C./0 hrs.

Similarly, for the sol generated at 135° C. and zero holding time, the calculated adsorption, assuming one adsorption site per acetate ion, is 0.0062 moles of adsorbent per gram of alumina, $Al_2O_3$. For the C.I. Direct Red 80, the anticipated adsorption would be approximately 8800 mg per gram of alumina. Although this is not found in freshly generated sols, "aged" sols of this material have shown adsorptions of 8000 mg per gram of alumina.

Thermal Analysis

1. Sample Prepared at 130° C./2 hrs.

The thermal residual weight of this compound on heating to 650° C. is calculated to be 65.66% for the compound resulting in alumina, $Al_2O_3$. The measured residual weight was found (FIG. 1) to be 69.50% without initial drying. It is suspected that some of the loosely bound acetate is lost as acetic acid at ambient conditions prior to the thermal analysis. For example, if it is assumed that only about half the moles of acetate are truly bonded to the alumina and the remainder is merely absorbed into the solids as acetic acid, the theoretical residual weight for heating $Al_2O_{2.91}(CH_3COO)_{0.17} \cdot 1.92H_2O$ is 70.27 percent.

1) Loss of loosely bound acetic acid and water:

$$Al_2O_{2.83}(CH_3COO)_{0.34} \cdot 2H_2O \rightarrow Al_2O_{2.91}(CH_3COO)_{0.17} \cdot 1.92H_2O + 0.17CH_3COOH$$

2) Sample heated to $Al_2O_{2.91}(CH_3COO)_{0.17} \cdot 1.92H_2O \cdot 650°$ C. $\rightarrow Al_2O_3$ This explanation is consistent with the adsorption of the direct Red 80 dye. For example, the amount of dye adsorbed would be predicted to be about 2400 mg per gram alumina.

Figure 2:
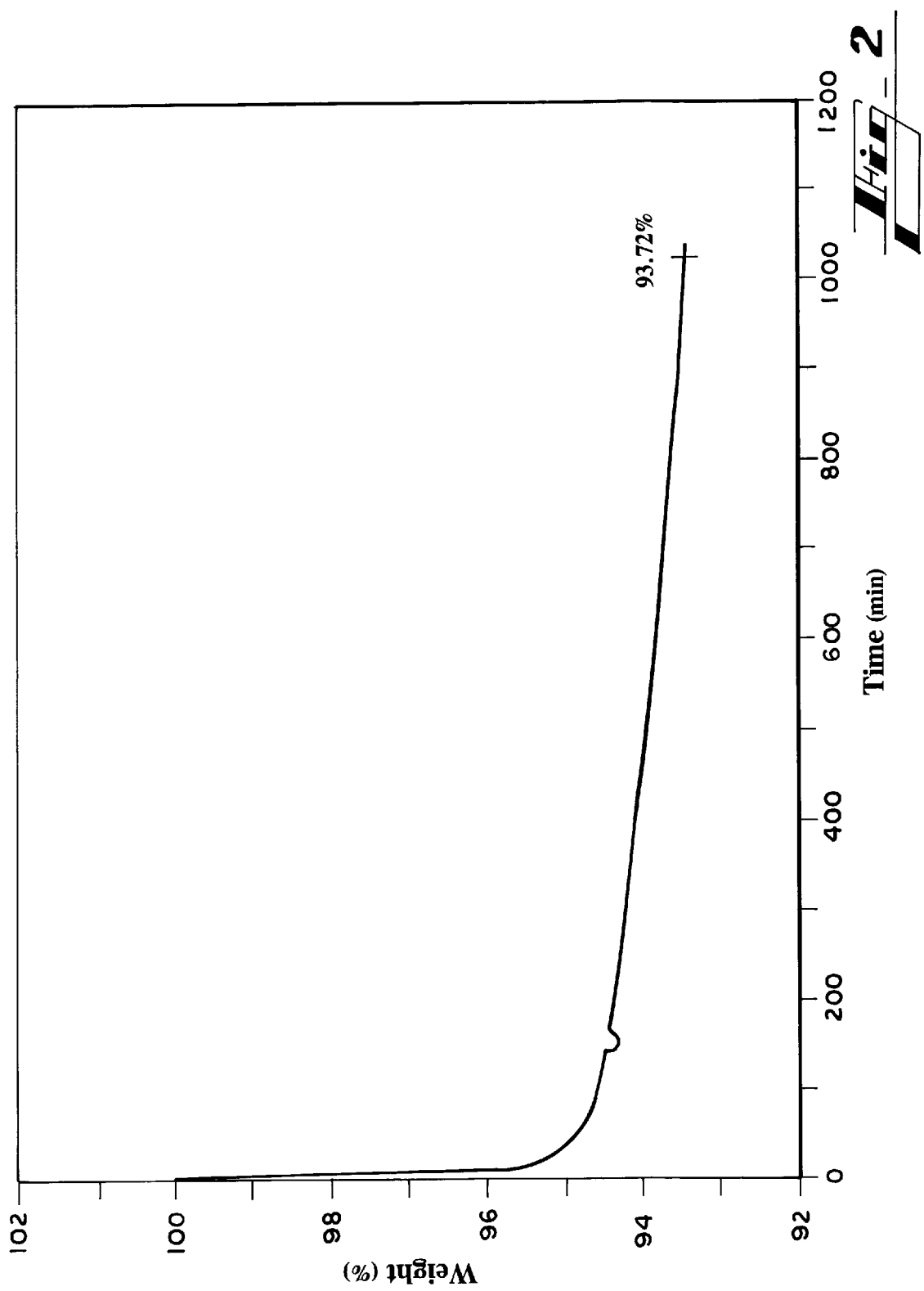
FIG. 2 shows the thermal residual weight of a sample of dried sol prepared at 140° C. for 2 hours when heated at 80° C. for 17 hours.
Figure 3:
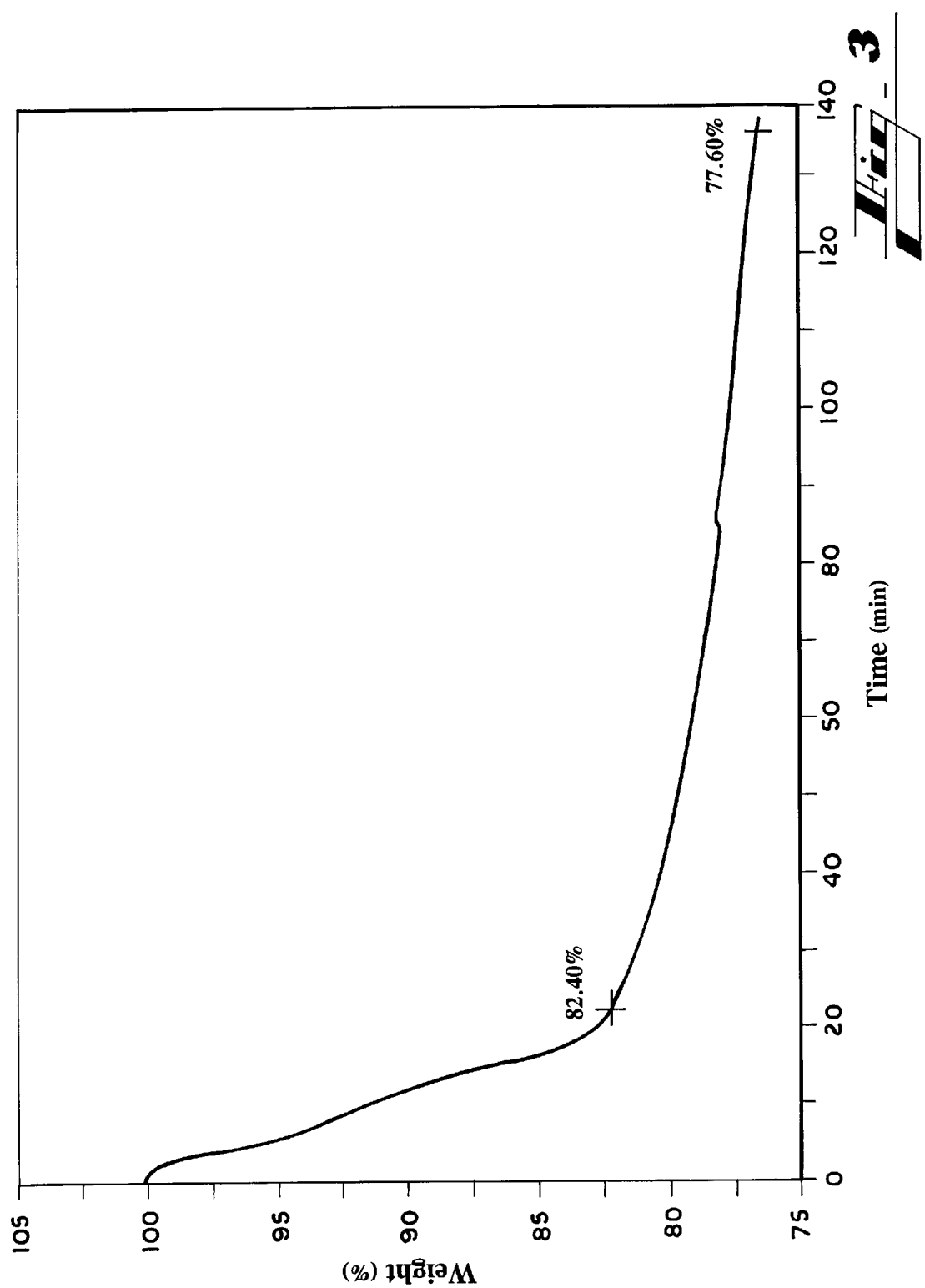
FIG. 3 shows the thermal residual weight of a sample of dried sol at 140° C. for 2 hours when heated at 350° C. for two hours.

Thus, additional samples were prepared by thermal treatment for characterization by infrared spectroscopy. To determine the nature of the chemical components being lost at 80° C., the sample of the dried sol was heated at 80° C. for 17 hours. The residual weight for this sample was measured as 93.72 percent (FIG. 2). Similarly, when a sample was heated at 350° C. for two hours a residual weight of 77.60 percent was determined (FIG. 3).

2. Sample Prepared at 135° C./0 hrs.

The air dried sample of the sol generated at 135° C. and zero holding time was examined by thermogravimetric methods. The maximum temperature that the sample was exposed to was 650° C. At that temperature only alumina would be anticipated to remain, as shown below:

$$Al_2O_{2.68}(CH_3COO)_{0.64} \cdot 2.25H_2O \rightarrow Al_2O_3$$

Figure 4:
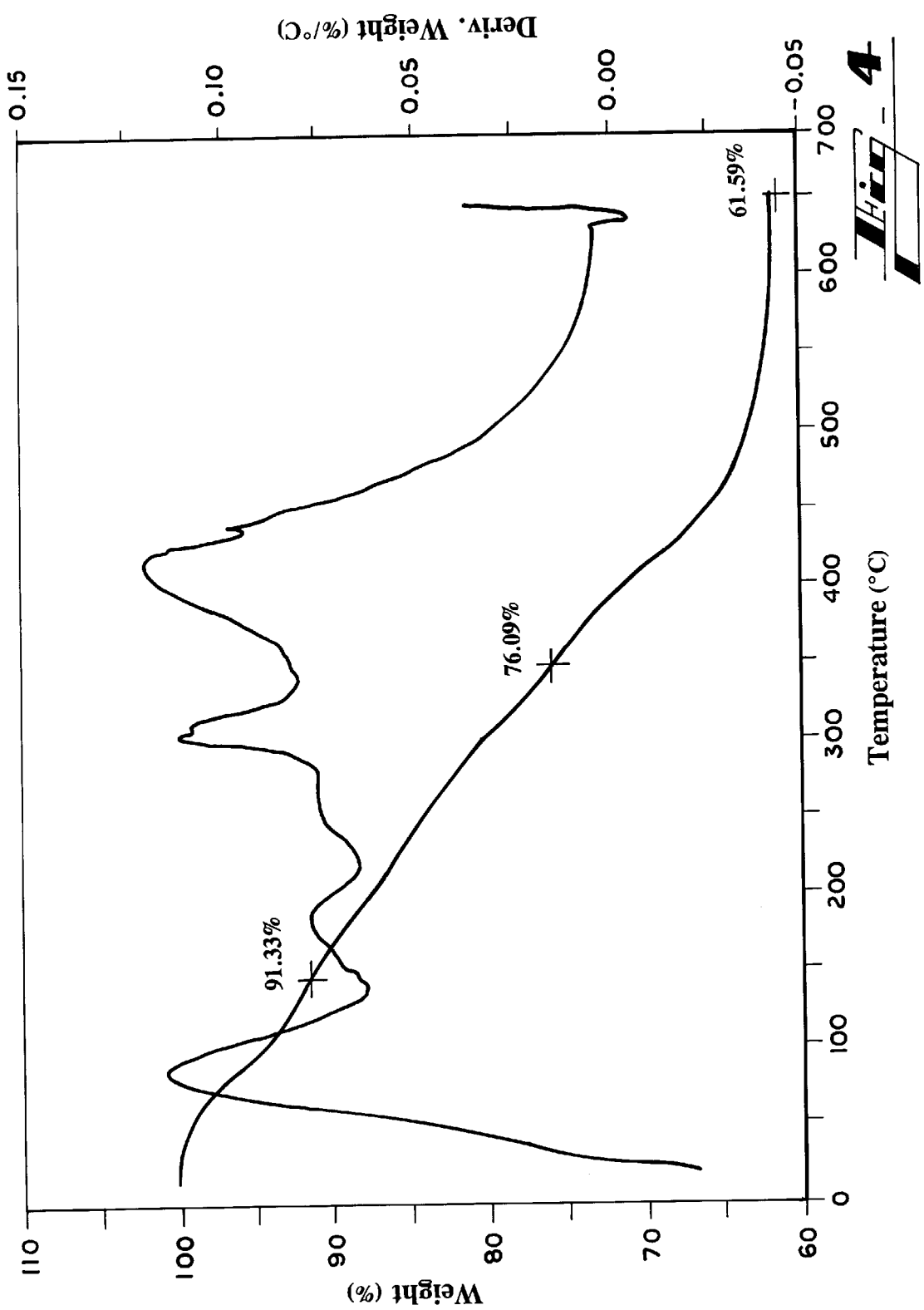
FIGS. 4 and 5 show the thermal residual weight of air dried samples of the sol generated at 153° C. and zero holding time for two temperature ramping speeds of 20 and 2 degrees per minute, respectively.
Figure 5:
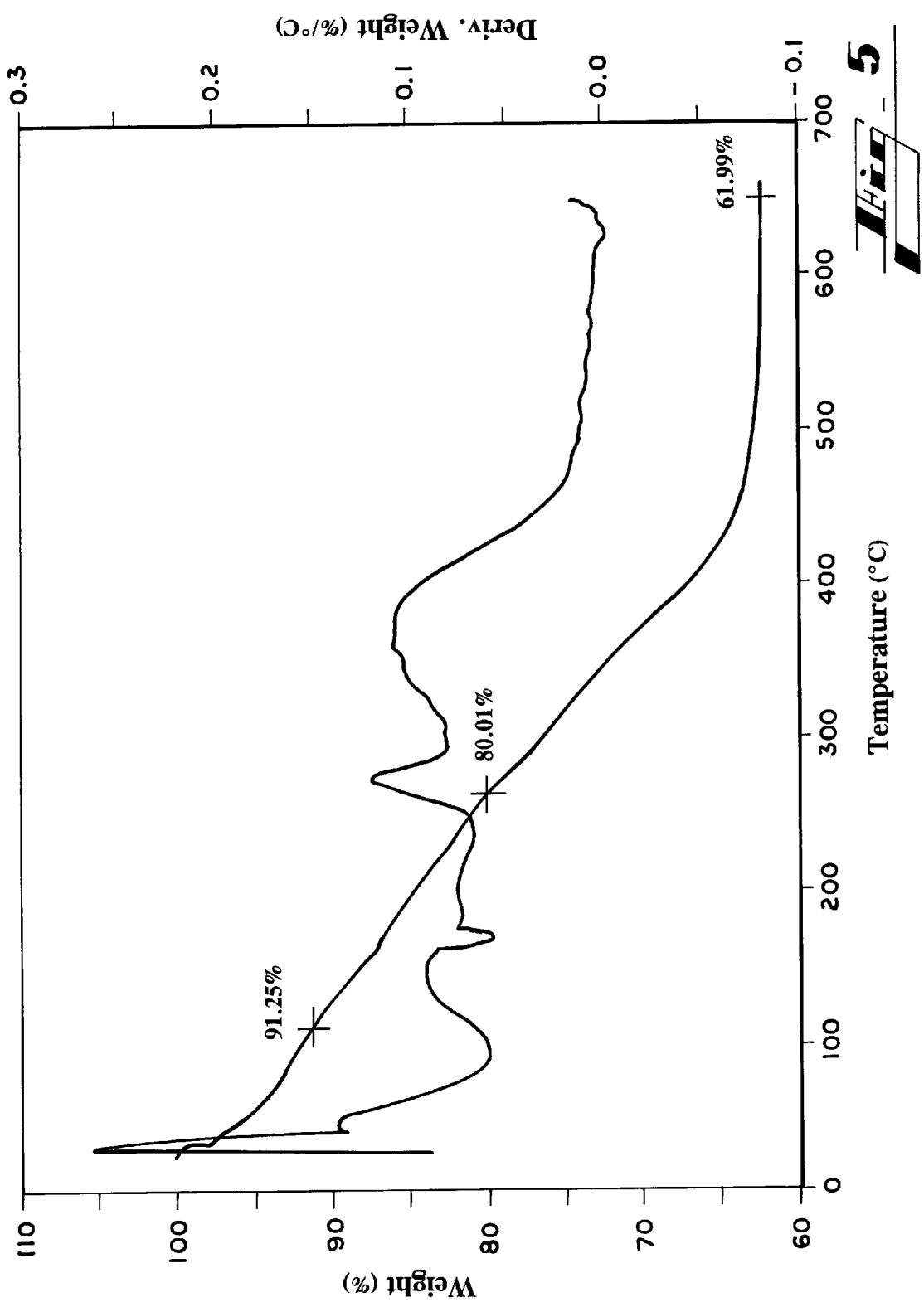

The calculated percent residual weight based on this equation is 58.24. As can be seen in FIGS. 4 and 5, for the two temperature ramping speeds of 20 and 2 degrees per minute, the percent residual weights were found to be 61.59 and 61.99, respectively.

Infrared Analyses

Figure 6:
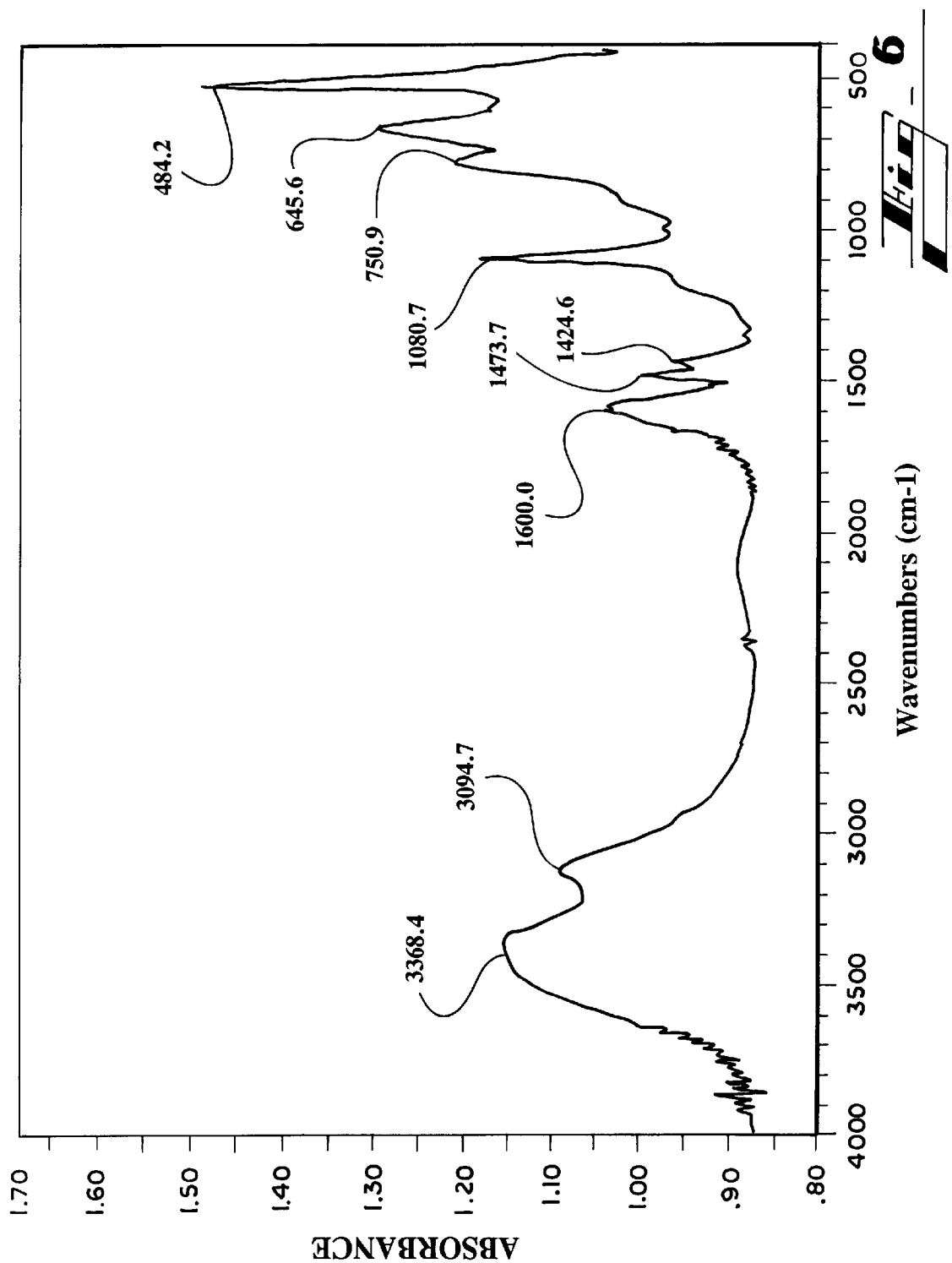
FIG. 6 shows the infrared spectra and the frequencies for absorbances of a sample generated at 153° C. and zero holding time when heated for 17 hours at 80° C.
Figure 7:
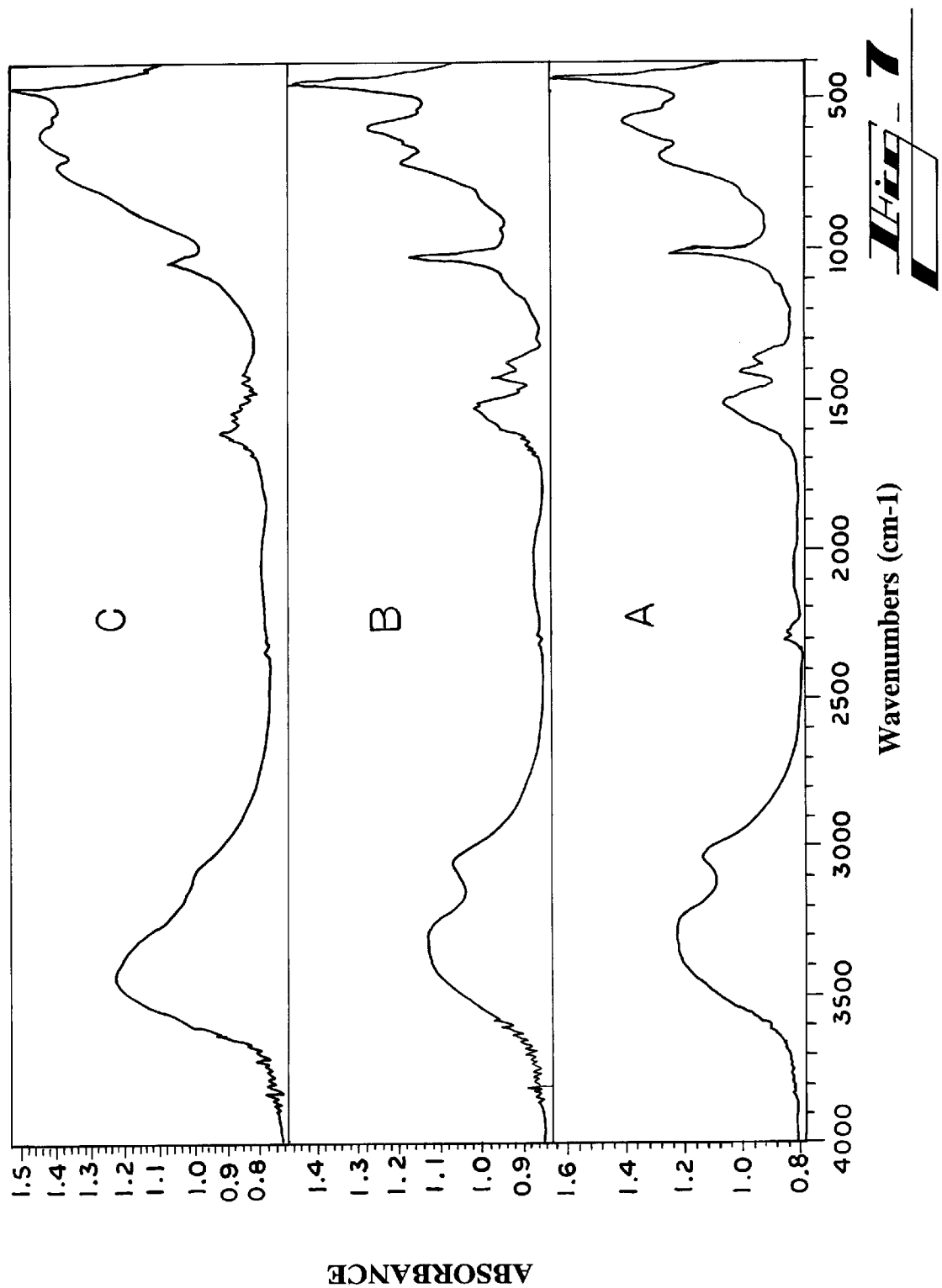
FIG. 7A shows the spectra of all the samples treated at 350° C. for 2 hours.
FIG. 7B shows the spectra of all the samples treated at 80° C. for 17 hours.
FIG. 7C shows the spectra of all the samples treated at room temperature.

The infrared spectra of samples of air dried AMS material were obtained using potassium bromide mulls. Spectra were obtained for the sample dried 1) at room temperature, 2) at 80° C. for 17 hours and 3) at 350° C. for 2 hours. The spectra, along with the frequencies for the absorbances, for the sample heated for 17 hours at 80° C. is shown in FIG. 6. The literature assignments for the various adsorptions are given below. Note that the ionized acetate salt is clearly shown at approximately 1600 cm$^{-1}$, giving further evidence that the AMS material is indeed an acetate salt or compound. The spectra of all samples are given in FIG. 7: A) treated at 350° C. for 2 hours, B) treated at 80° C. for 17 hours and C) the air dried at room temperature. As can be seen in all the spectra, the salt structure is present.

| FREQUENCIES (cm$^{-1}$) | ASSIGNMENTS | MODE | REFERENCES |
|---|---|---|---|
| 3370 | —OH, —COOH | stretching | 1 |
| 3090 | —OH (Boehmite) | stretching | 1, 2 |
| 1580 | Ionized carboxyl (salt) | antisymmetrical | 1 |
|  | C—O Stretching in —C—O—Al | stretching | 3 |
| 1474 | CH$_3$—(C=O) | stretching | 1 |
| 1425 | Ionized carboxyl (salt) | stretching | 1 |
| 1070 | —OH (boehmite) | bending | 1, 2, 4 |
| 750 | —OH (boehmite) | bending | 2 |
| 640 | Al—O | stretching | 2, 4 |
| 480 | Al—O | stretching | 2, 4 |

1 Handbook of Chemistry and Physics; Lide, D.R.; Ed.-in-Chief, 73rd ed.; CRC Press, 1993; 9–152.
2 The Infrared Spectra of Minerals; Farmer, V.C., Ed.; Mineralogical Society, 1974.
3 Maksimov, V.N.; Grigor'ev, A.I.J. Inorg. Chem. USSR (Engl. Transl.) 1964, 9(4), 559–560.
4 Infrared Spectra of Inorganic Compounds; Nyquist, R.A.; Kagel, R.O., Ed; Academic Press, 1971.

As is seen from the TGA (FIG. 1), considerable weight loss (16.16%) occurs above 350° C. The weight loss measured above 350° C. is the salt given by the following empirical formula, $Al_2O_{2.91}(CH_3COO)_{0.17} \cdot 0.085H_2O$, the theoretical weight loss is calculated as 13.24 percent, which is in good agreement with that measured. Thus, only water is lost at these temperatures and the alumina acetate salts remain relatively intact.

X-Ray Diffraction

1. Sample Prepared at 130° C./2 hrs.

Figure 8:
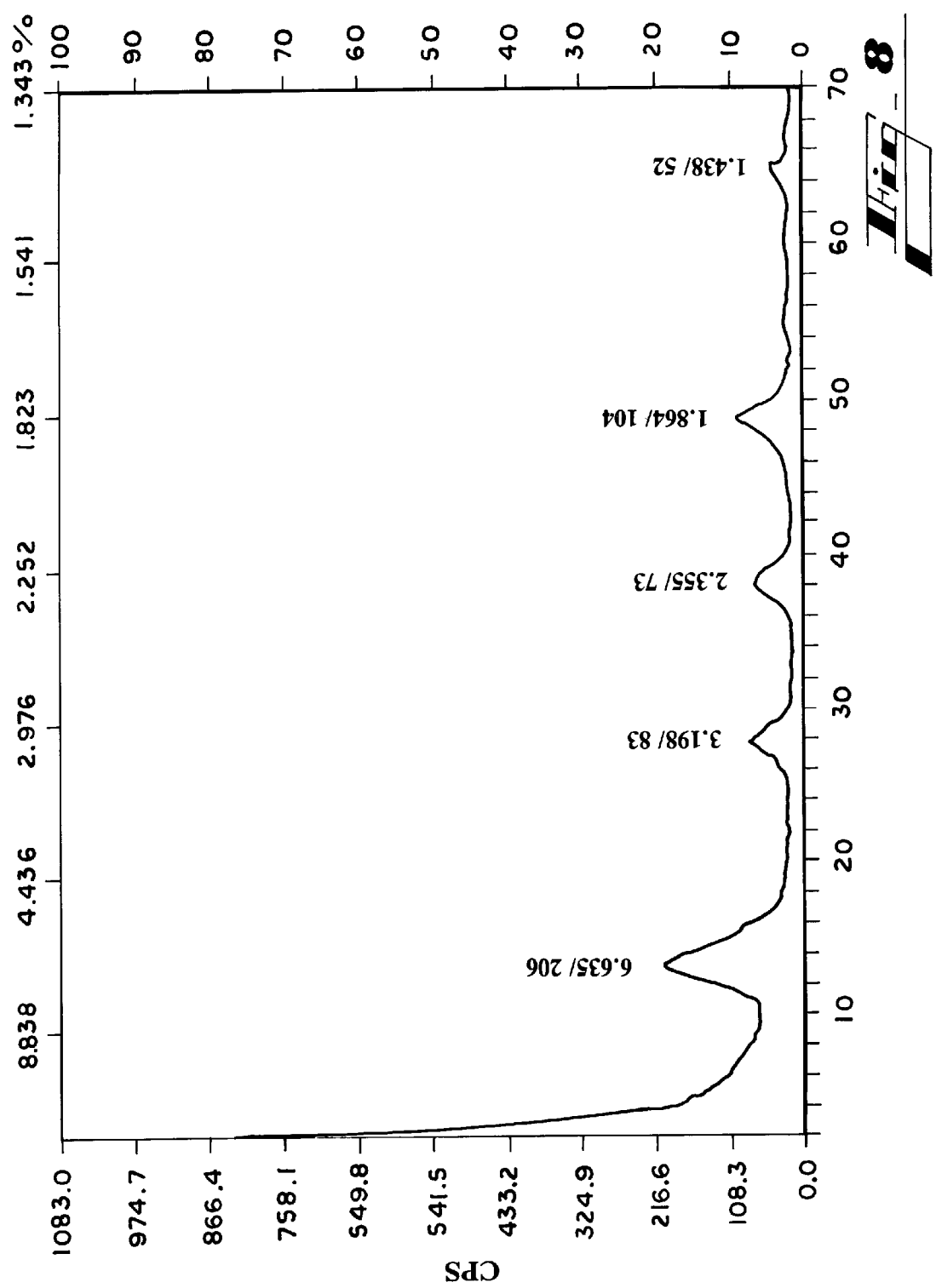
FIG. 8 shows a diffractogram of AMS sol prepared at 140° C. for 2 hours dried at 25° C.

The X-ray diffraction of the air dried at 25° C., AMS sol prepared at 130° C. for 2 hours as a 3.0 percent alumina sol showed broad lines consistent with boehmite alumina. The diffractogram is shown in FIG. 8. The line broadening is due to the small particles of alumina present in the sample. The d-spacing lines for the AMS sol and the literature values are given below. The major difference observed is found in the first peak at 2-theta of about 14 degrees, e.g. at the d-spacing of 6.635 angstroms versus 6.110 for the literature value of boehmite. This, of course, would be expected if the acetic acid were clearly bonded to the alumina fiber, e.g. a salt complex.

Figure 9:
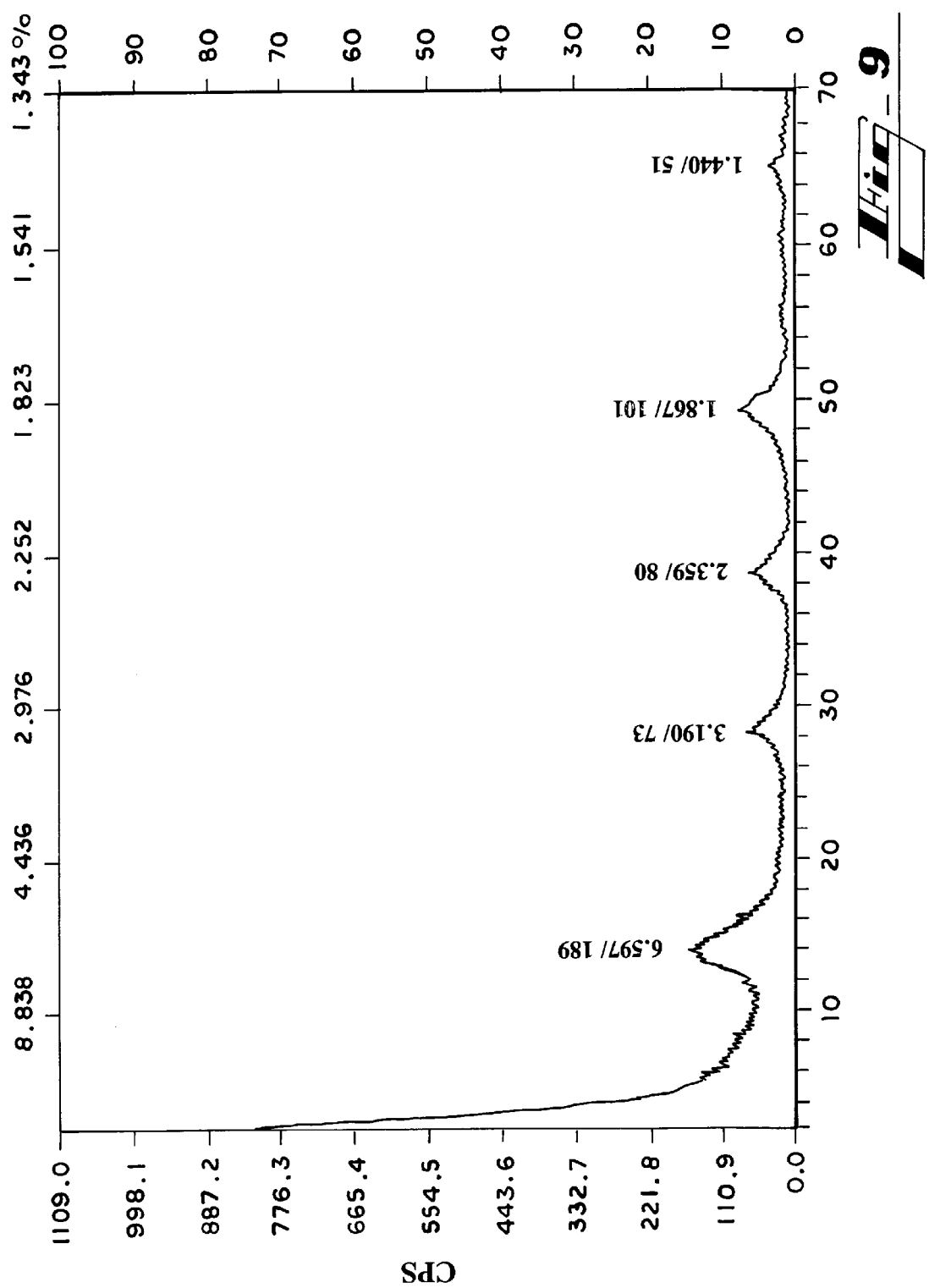
FIG. 9 shows a second diffractogram of AMS sol prepared at 140° C. for 2 hours dried at 25° C.
Figure 10:
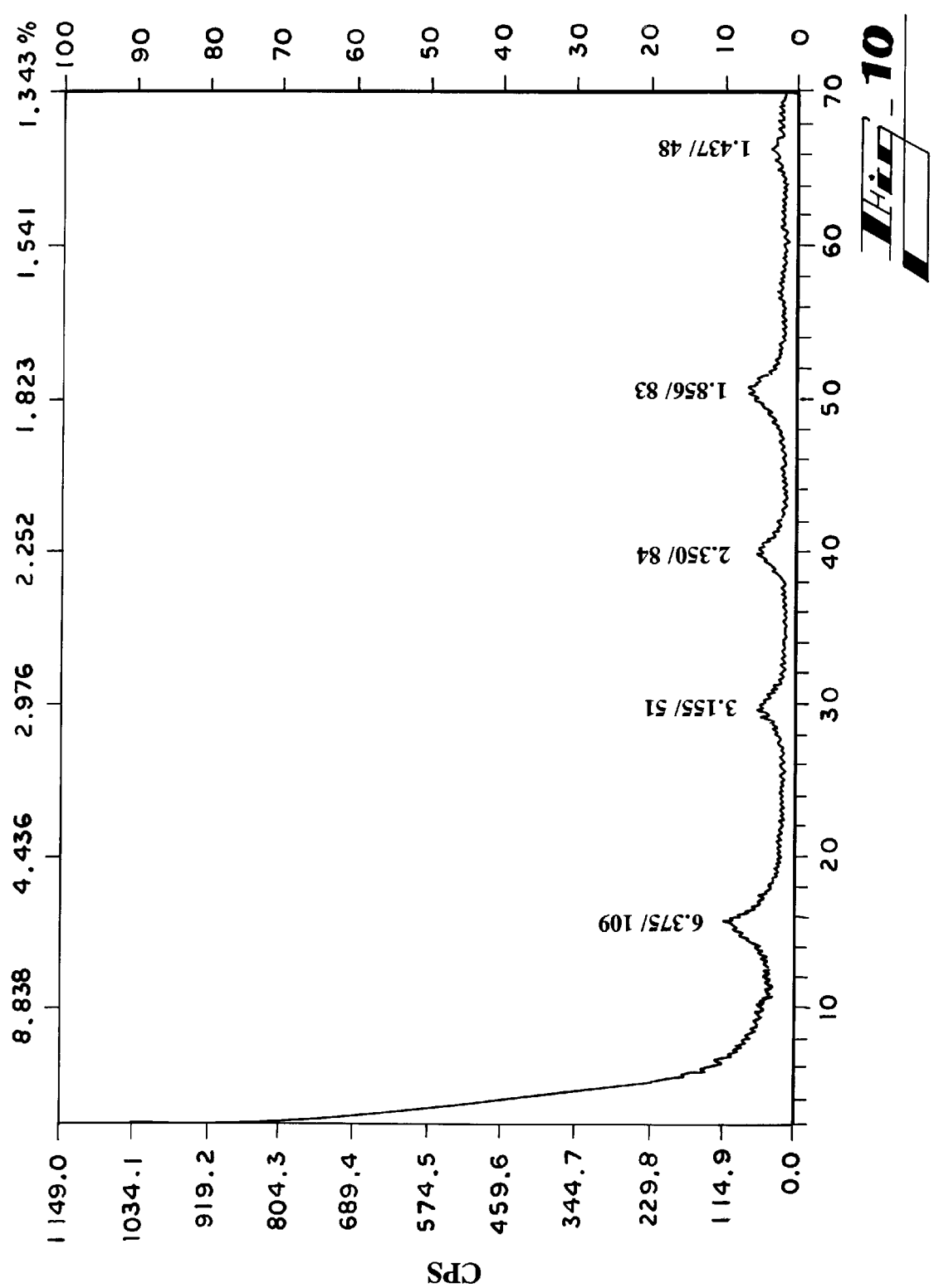
FIG. 10 shows a diffractogram of AMS sol prepared at 140° C. for 2 hours dried at 80° C.

To further explore this peak at d=6.635 A, a second diffractogram was run to verify the d-spacings. As shown in FIG. 9, the identical diffraction was obtained. However, when the sample was dried at 80° C., the d-spacing at 6.6 angstroms moved to 6.375 A (FIG. 10), toward that for boehmite. This suggests this salt complex does undergo a thermal reaction at 80° C., consistent with other experimental findings. All these diffraction results are summarized below:

| 130° C./2 Hours Dried | | 135° C./0 Hours | Boehmite, |
|---|---|---|---|
| 25° C. | 80° C. | 25° C. | AlOOH: literature values |
| 6.635/6.597 | 6.375 | 6.835 | 6.110 |
| 3.198/3.190 | 3.155 | 3.172 | 3.164 |
| 2.355/2.359 | 2.350 | 2.332 | 2.346 |
| | | | 1.980 |
| 1.864/1.867 | 1.856 | 1.861 | 1.860 |
| | | | 1.850 |
| | | | 1.770 |
| | | | 1.662 |
| | | | 1.527 |
| | | | 1.453 |
| 1.438/1.440 | 1.437 | 1.434 | 1.434 |
| | | | 1.383 |

Figure 11:
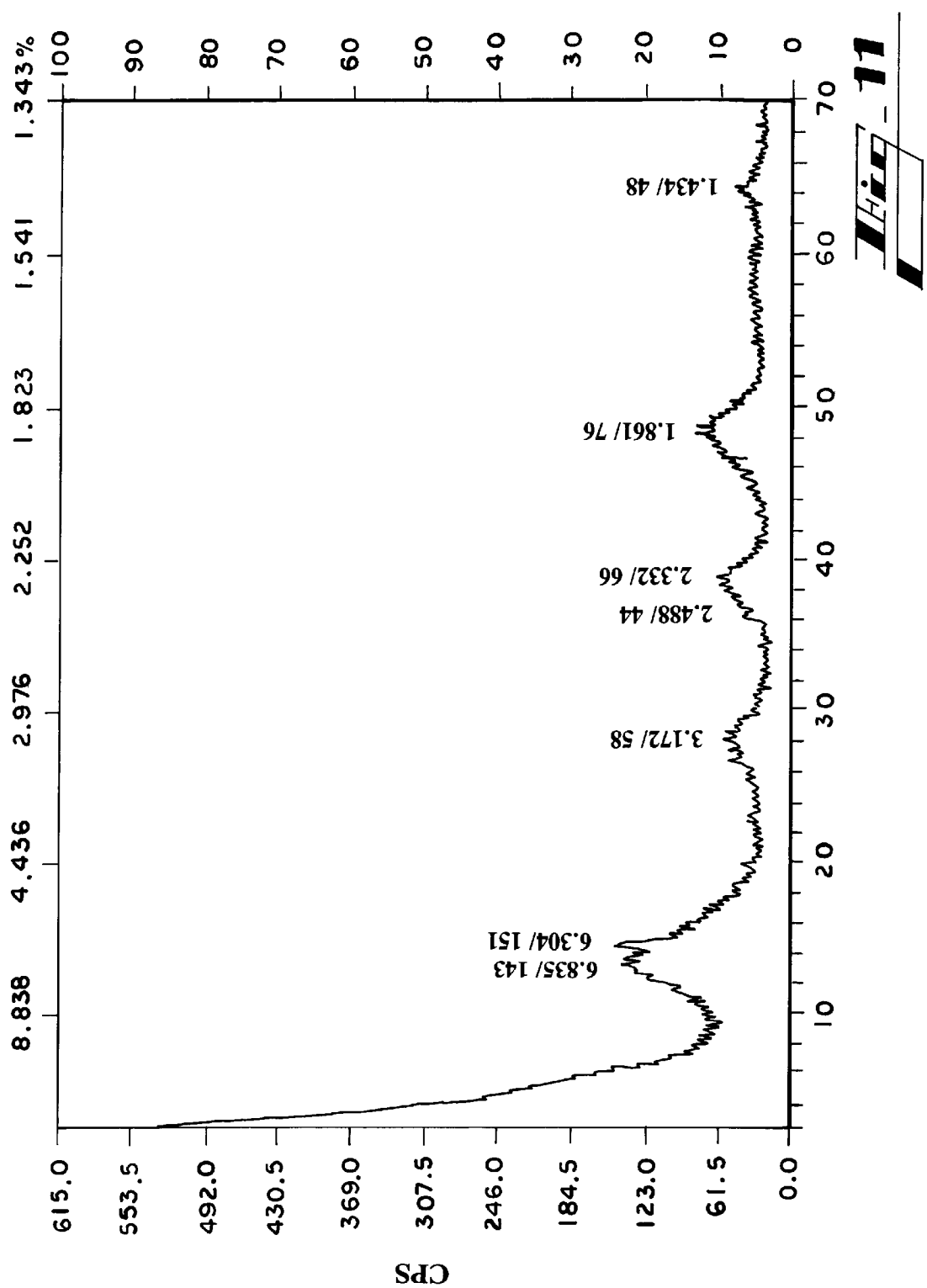
FIG. 11 shows a diffractogram for dried sample prepared at 153° C. with zero holding reaction time dried at 25° C.

For the dried sample prepared at 135° C. with zero holding reaction time, several other small peaks are observed in the diffractogram (See FIG. 11). The most important shift from boehmite alumina occurs at about 6.8 angstroms and appears to be unique for this alumina acetate salt/complex.

Elemental analyses, thermal studies, infrared spectroscopy, and X-ray diffraction support the fact that the sol solids are comprised of a unique boehmite alumina acetate salt, having a high degree of cationic charge, or acetate to alumina ratio. The empirical formulae for products prepared at 130° C. for 2 hours and at 135° C. with zero hours reaction time and air dried at ambient temperatures, are best fit by $Al_2O_{2.83}(CH_3COO)_{0.34} \cdot 2H_2O$ and $Al_2O_{2.68}(CH_3COO)_{0.64} \cdot 2.25H_2O$. These formulae are further consistent with dye adsorption studies, thermogravimetric analyses and infrared spectroscopy.

Examples 1,2,3 and 4 follow the procedure disclosed in U.S. Pat. No. 3,207,578. Example 1 and 2 follow Example 1 of patent number 3,207,578

EXAMPLE 1

A 1 liter 316 stainless steel autoclave reactor fitted with a heating jacket supplied with oil from an external heater, a thermocouple, a pressure gauge, an efficient turbine stirring and a runoff valve was charged 380g demineralized water, 84.5 g basic aluminum acetate and 0.83 g of anhydrous ammonium sulphate. The reactor was sealed and the agitator started. The oil was preheated to 174° C. then applied to the heating jacket. The internal temperature of the contents rose to 160° C. over 23 minutes and was held at that temperature for 20 minutes. The oil was cooled by means of inserting a water cooling coil into the oil flow and the reactor contents cooled to 30° C. in 12 minutes. The thick product liquid was withdrawn.

EXAMPLE 2

The same equipment as described in Example 1 was charged 451 g demineralized water, 49 g basic aluminum acetate and 0.49 g anhydrous ammonium sulphate. The same procedure and temperature profile of Example 1 was followed.

Examples 3 and 4 follow Example 2 of U.S. Pat. No. 3,207,578.

EXAMPLE 3

To the same equipment as described in Example 1 was charged 435 g demineralized water, 65 g basic aluminum acetate and 0.69 g anhydrous sodium sulphate. The reactor was sealed and the agitator started. Oil preheated to 173° C. was applied to the reactor jacket and the internal temperature rose to 160° C. within 21 minutes. The reactor temperature was held at 160° C. for 1 hour then cooled by inserting a cooling coil in the oil circulation. The reaction mix was cooled to 29° C. in 12 minutes.

EXAMPLE 4

In the same equipment as described in Example 1 and following the same procedure as set forth in Example 3, a reaction mixture comprising 451 g demineralized water, 49 g basic aluminum acetate and 0.69 g sodium sulphate (anhydrous) was processed.

TABLE 1

| Example | 1 | 2 | 3 | 4 |
|---|---|---|---|---|
| Dye Uptake (mg/g) | 1217 | 879 | 878 | 878 |
| A1203 % w/w | 5.27 | 2.61 | 3.4 | 2.83 |
| BET surface area m$^2$/g solid | 200.8 | 206.4 | 164.9 | 161.2 |
| Zeta potential | 33.98 | 32.6 | 29 | 29.56 |
| Charge density (Zeta/BET) | 0.17 | 0.16 | 0.18 | 0.18 |
| Acetate content % w/w | 14.3 | 11.3 | 12.0 | 11.8 |
| Aluminum % w/w | 40.05 | 41.91 | 40.1 | 41.65 |
| Aluminum/Acetate weight ratio | 2.8 | 3.7 | 3.3 | 3.6 |

Examples 5, 6, 7 and 8 are a series of reactions at a reaction temperature of 130° C. The procedure followed is set forth below, each example differing by the time at which reaction temperature was held.

To a 1l stainless steel pressure reactor was added 49 g basic aluminum acetate and 451 g demineralized water. The reaction contents were heated to reaction temperature using preheated oil and after reaction time had elapsed was cooled by applying cooling water to the heating oil circuit.

TABLE 2

| Example | 5 | 6 | 7 | 8 |
|---|---|---|---|---|
| Time at 130° C. (mins) | 10 | 15 | 30 | 60 |
| Dye Uptake (mg/g) | 10300 | 6900 | 3100 | 2100 |
| Zeta | 33.5 | 36.3 | 39.0 | 45.5 |
| BET | 5 | 8 | 62 | 140 |

TABLE 2-continued

| Example | 5 | 6 | 7 | 8 |
|---|---|---|---|---|
| Charge Density | 6.7 | 4.5 | 0.62 | 0.32 |
| Acetate content % w/w | 42.3 | 25.8 | 16.4 | 13.1 |

EXAMPLE 9

To a 75 liter 316 stainless steel reactor fitted with an oil heating jacket and internal cooling coils was added 50.12 kg tap water and 2.88 kg basic aluminum acetate. The reactor was closed and heating applied to raise internal temperature to 128° C. over 1 hour 19 minutes. The reactor temperature was held between 128 and 133° C. for 1 hour then contents cooled to 47° C. over 1 hour. The translucent product was discharged. The product had the following properties; Dye Update 2700 mg/g, acetate content of solid 20.65% w/w.

EXAMPLE 10

The procedure described in Examples 5 to 8 was followed except that the reaction temperature was 140° C. and the reaction time at that temperature was 15 minutes. The product produced had a Dye Uptake of 1900mg/g and an acetate content in the solid of 39% w/w.

EXAMPLE 11

A sol was diluted with deionized water to 0.75% w/w concentration alumina and thoroughly mixed. The fabric was weighed before and after treatment to obtain the percent weight pick up. The target pick up was 80 percent of the original pre-treatment weight. The fabric was dried in an oven at 50° C. and then dyed in a solution containing 1 gram of dye per liter of solution at ambient temperature. After dyeing, the fabric was placed into the oven to dry and compared visibly to the commercial control (90° C., 10wt. % NaCl) for intensity and even coloration.

After dyeing fabric with the sols generated in Example 5, certain types of sols gave noticeably superior dye adsorption than others. The sols, prepared at 130° C./2 hours and containing 3% $Al_2O_3$ and comprised of short, thin fibers produced the most promising dye adsorption. These fabric samples were analyzed by reflectance spectroscopy commonly used in the textile industry. It was necessary to obtain a K/S value, which is used in the textile field as a standard for dye intensity. Kubella-Munk's constant, K/S, is an indicator of a substrate's depth of shade where K is an absorption coefficient and S is a scattering coefficient, see AATCC Evaluation Procedure 6, 1996, AATCC Technical Manual 1996. The K/S values obtained from the fabric that was treated with the short, thin fibers (ex. runs 6 and 22) and dyed was 6.368. The value for a simulated commercially dyed product (e.g., 10% salt at 90° C.) was 5.346, therefore, the addition of the aluminum monohydrate sol improved the intensity of the dye on fabric. The reflectance testing procedure is a standard (ASTM) procedure used in the textile industry. By using this test and interpolating the data obtained, it can be determined whether a product or additive enhances the fabric significantly enough to be commercially marketable.

The dye concentration of the supernatant can be determined by using the absorbance obtained and the standard plot. The amount of the dye adsorbed by the sol is the difference between the starting amount of the dye and the amount left in the supernatant. For example, if the diluted supernatant from centrifugation is found to have a concentration of 0.040 mg of dye per gram of the solution, then the ability of this sol to adsorb this dye can be calculated as follows:

| amount of excess dye: | 0.040 mg/g × 60 × 200 g – 480 mg |
|---|---|
| amount of dye adsorbed: | 600 mg – 480 mg = 120 mg |
| adsorption capacity: | 120 mg/0.20 g – 600 mg/g | where 0.040 mg/g is the dye concentration of the diluted supernatant obtained from the standard plot, 60 is the dilution factor for the supernatant, the 200 g is the total weight of the mixture, 600 mg is the starting amount of the dye, and 0.20 g is the amount of AlOOH solid used. The result of this example is that one gram of AlOOH solid is able to adsorb 600 mg of this dye.

TABLE 3

FABRIC DYEING EXPERIMENTS

| Run Number | Initial Wt., g | Wet Wt. After Sol, g | g of Sol | % of Pick Up | Reflectance Run/Control Ratio |
|---|---|---|---|---|---|
| Commercial Control | — | — | — | — | 1.00 |
| 1 | 6.72 | 12.48 | 5.76 | 85.71 | 1.02 |
| 2 | 6.59 | 12.24 | 5.65 | 85.74 | 1.09 |
| 3 | 5.66 | 10.31 | 4.65 | 82.16 | 1.00 |
| 4 | 5.56 | 10.05 | 4.49 | 80.76 | 0.81 |
| 5 | 6.27 | 11.89 | 5.62 | 89.63 | 0.80 |
| 6 | 5.13 | 9.25 | 4.12 | 80.31 | 1.19 |
| 7 | 6.35 | 11.83 | 5.48 | 86.30 | 0.96 |
| 8 | 6.65 | 12.52 | 5.87 | 88.27 | 0.90 |
| 9 | 5.81 | 10.99 | 5.18 | 89.16 | 0.75 |
| 10 | 5.85 | 10.75 | 4.90 | 83.76 | 0.78 |
| 11 | 5.81 | 10.98 | 5.17 | 88.98 | 0.99 |
| 12 | 6.20 | 11.34 | 5.14 | 82.90 | 0.52 |
| 13 | 6.35 | 11.54 | 5.19 | 81.73 | 0.56 |
| 14 | 6.03 | 11.04 | 5.01 | 83.08 | 0.86 |
| 15 | 6.42 | 11.37 | 4.95 | 77.10 | 0.92 |
| 16 | 6.65 | 11.95 | 5.30 | 79.70 | 0.67 |
| 17 | 6.02 | 10.61 | 4.59 | 76.25 | 0.55 |
| 18 | 5.56 | 10.15 | 4.59 | 82.55 | 0.70 |
| 19 | 7.08 | 12.78 | 5.70 | 80.51 | 0.94 |
| 20 | 6.44 | 12.56 | 6.12 | 95.03 | 0.98 |
| 21 | 6.83 | 12.72 | 5.89 | 86.24 | 0.74 |
| 22 | 6.79 | 12.35 | 5.56 | 81.89 | 1.15 |
| 23 | 6.28 | 11.31 | 5.03 | 80.10 | 0.67 |
| 24 | 6.37 | 11.37 | 5.00 | 78.49 | 1.05 |
| 25 | 6.49 | 12.43 | 5.94 | 91.53 | 0.71 |
| 26 | 7.45 | 13.49 | 6.04 | 81.07 | 0.95 |
| 27 | 7.30 | 13.48 | 6.18 | 84.66 | 0.98 |

Adsorption from Spent Dye Baths

The general procedure for a dye adsorption experiment normally includes six steps:
1) establishing standard Beer's law plot
2) preparing dye solutions and, for reactive dyes only, hydrolysis of the dyes
3) mixing sols with dye solutions
4) separating the dye-adsorbed particle from water
5) determining the amount of excess dye
6) calculating the amount of dye adsorbed to obtain adsorption capacities.

Preparation of Standard Plot

The maximum absorbencies of six known concentration dye solutions were first obtained using UV-Vis spectroscopy. For the values obtained and the corresponding concentrations (mg of dye per gram of total solution), a plot of absorbencies versus concentrations was generated. The quality of the experimental plot was checked and a best-fit line was produced by computer. This line was used for excess dye determination.

Preparation of Mixture of Sol and Dye Solution

Typically, the total weight of the mixture as well as the amount of each component, including dye, sol, 0.1% Polyacrylamide (PAA), and water, are determined before any experiment. The sequence of addition into the container is: dye, water, sol, and PAA. The dye has to be completely dissolved, however, before the sol can be added. In the cases of reactive dyes, hydrolysis of the dye is a necessary step before the addition of the sol.

Determination of Excess Dye

About 50 ml of the mixture was centrifuged (or filtered) at the maximum velocity for 2.5 hours. The supernatant was then diluted 20–120 times (by weight) for the UV-Vis experiment. The dilution used depends on the absorbencies range of the standard plot, normally between 0.2–1.5.

Table 3 summarizes the cloth dyeing experiments and indicates that short thin fibers give superior dye adsorption onto the cloth. Run number 6 shows the highest reflectance value; therefore, the best type of fibers to use are, for this purpose, the thin fibers.

EXAMPLE 12

The flocculation technology in the textile coloration industry involves materials that can adsorb a large quantity of dye and the dye-adsorbed particle can be separated from water easily. For a material to qualify as a flocculating agent, a minimum dye absorption capacity of 200 mg per gram of solid is required.

A screening test was done to evaluate the dye adsorption abilities of the 27 sol products obtained from Example 5. The experiments were designed to mix the same amount of the dye with the 27 sol solutions having the same solid concentration. The reduction of the concentration of the dye caused by adsorption of fibrous acetate is then judged by the changes of the absorbencies obtained from UV-Vis spectroscometer. In these tests, 10 ml of sol solution (0.75% $Al_2O_3$ concentration) was mixed with 0.5 ml of dye (C.I. direct red 80) solution of 1 g/L concentration in a 15 ml centrifuge tube. After 2 hours centrifugation, the supernatant was scanned, using a Perkin-Elmer Lamda 2 UV-Vis spectrophotometer. The absorbencies of screening tests are listed in Table 4.

TABLE 4

ABSORBANCE VALUES OBTAINED FROM DYE ABSORPTION TESTS

| Run Numbers | Absorbance |
| --- | --- |
| (Control) | 1.543 |
| 1 | 0.2008 |
| 2 | 0.9432 |
| 3 | 0.151 |
| 4 | n/a* |
| 5 | n/a* |
| 6 | 0.170 |
| 7 | n/a* |
| 8 | n/a* |
| 9 | 0.1074 |
| 10 | 0.096 |
| 11 | 0.2439 |
| 12 | n/a* |
| 13 | n/a* |
| 14 | n/a* |
| 15 | 0.0895 |

TABLE 4-continued

ABSORBANCE VALUES OBTAINED FROM DYE ABSORPTION TESTS

| Run Numbers | Absorbance |
| --- | --- |
| 16 | 0.1113 |
| 17 | 0.1848 |
| 18 | 0.1007 |
| 19 | 1.0513 |
| 20 | 0.7695 |
| 21 | 0.0897 |
| 22 | 0.4112 |
| 23 | 0.0686 |
| 24 | 0.1629 |
| 25 | n/a* |
| 26 | 0.4376 |
| 27 | 0.1973 |

*n/a - minor absorption that can not be distinguished from the background

The data in Table 3 and Table 4 shows that while the smaller fibers might adsorb dye better (good results on cloth dyeing experiments), the resulting particles may be too small to be removed from water easily (poor settling rate). A sol product with a high percentage of large bundle was thus chosen for initial adsorption capacity tests reported in this example, taking advantage of the rapid settlement of these bundles. Sol of this type is produced with 3% $Al_2O_3$, relatively high reaction temperature (135° C.) and long reaction time (over 5 hours).

Experiments were conducted to identify the adsorption capacity of the alumina acetate sol for various dyes. For a typical experiment, 0.600 and 0.500 g of dye was dissolved into 193.73 and 193.83 g of $H_2O$, respectively. To each dye solution, 5.67 g of sol was added to make the total mixture weight of 200.00 g which was well mixed by shaking the container. A portion of the mixture was then centrifuged for 2.5 hours. For reactive dyes, 45 minutes of a hydrolysis process at 140° F. in the pH range of 10.5–11.0 was performed before addition of sol. The sols used were prepared purposely to have a high percentage of large bundles. They were prepared using the parameters of Example 5 except for a much longer reaction time of five hours instead of 2.

Before the addition into the dye solution, the alumina acetate monohydrate salt sol is stirred by a magnetic bar for ten minutes or more to ensure the homogeneity. Typically, 5.67 g of this sol, which equals 0.20 g of alumina acetate monohydrate fiber was used. The following calculations were used:

| | | |
| --- | --- | --- |
| Total amount of $Al_2O_3$ solid: | 0.03 × 1500 g | = 45.00 g |
| Total amount of $Al_2O_3 \cdot H_2O$ solid: | (120 g/102 g) × 45 g | = 52.94 g |
| % solid as $Al_2O_3 \cdot H_2O$: | (52.94 g/1500 g) × 100% | = 3.35% |
| or: | 5.67 g × 0.0353 | = 0.200 g |

To determine the dye adsorption, the excess (unadsorbed) dye was measured using visible spectroscopy. A standard Beer's law plot (absorbencies vs. dye concentration) was first prepared using dye solutions with known concentration. The supernatant resulting from centrifuging the mixture of sol and dye solution was diluted 20–60 times. The excess dye concentration was calculated from the UV-Vis absorbance, based on a standard plot prepared earlier. The amount of dye adsorbed was determined by comparing the reduction in dye concentration. For example, if the starting dye concentration was 3 g/L and the excess dye concentration was 2 g/L, then 1 g of dye was adsorbed by the given amount of sol. The absorption capacity was reached when the amount of dye adsorbed became relatively unaffected by the starting dye concentration.

Capacity tests for 5 dyes and results are summarized in Table 5.

TABLE 5

AMOUNT OF DYE ABSORBED (mg) WITH AMS CONTAINING A HIGH PERCENTAGE OF BUNDLES (Run 1)

| | Dye Type | | | | |
|---|---|---|---|---|---|
| | Direct | Direct | Basic C.I. Name | Acid | Sulfur |
| | Yellow 106 | Red 80 | Red 14 | Black 194 | Black 1 |
| Conc. #1 | 492 | 688 | 0 | 345 | 468 |
| Conc. #2 | 520 | 672 | 54 | 305 | 528 |

Conc. #1 and #2 are the starting concentrations of 2.5 and 3 g/L, respectively.

One concern was the ability to reproduce the sol products. A second batch of alumina acetate sol (Run 2) was made using the reaction parameters of Run 1. Table 8 compares the results of the two sol products prepared using the same reaction parameters.

TABLE 6

AMOUNT OF DYE ABSORBED (mg) WITH DIFFERENT ALUMINA SOLS

| | Dye Type | | | | |
|---|---|---|---|---|---|
| | Direct | Direct | Basic C.I. Name | Acid | Sulfur |
| | Yellow 106 | Red 80 | Red 14 | Black 194 | Black 1 |
| Run 1 | 520 | 672 | 54 | 305 | 528 |
| Run 2 | 484 | 564 | 84 | 319 | 588 |

In some cases, NaCl or $Na_2SO_4$ was used to simulate the production environment. The results are presented in Table 7.

TABLE 7

THE EFFECT OF SALTS ON THE ABSORPTION CAPACITY

| Direct Dyes (3 g/L) | NaCl 1% | NaCl 0.5% | $Na_2SO_4$ 1% | $Na_2SO_4$ 0.5% |
|---|---|---|---|---|
| C.I. Red 80 | 636 | 565 | 414 | 414 |
| C.I. Yellow 106 | 604 | 520 | 568 | 586 |

EXAMPLE 13

This experiment tested adsorption at a pH of 3, 4, and 5 in order to determine which pH yielded the most adsorption of dye.

Dye solutions were prepared at concentrations of 100 mg/L and the pH adjusted with concentrated HCl or with sodium carbonate ($Na_2CO_3$), the amount and type of adjustment was determined by earlier experimentation. Alumina acetate sol fiber diluted 60 times and 0.1% PAA were added and the samples centrifuged.

The sols used in Examples 14, 15, 16, 17, and 18 were prepared using the same reaction parameters as run #6 in the experimental design presented in Example 5. Oftentimes, a dilution of this sol was made to enhance the dispersion of the alumina acetate fibers into the dye solution.

TABLE 8

| C.I. NAME | RUN NUMBER | ADSORPTION (mg/g) | pH |
|---|---|---|---|
| Direct Red 80 | 1 | 2080 | 3.01 |
| Direct Red 80 | 2 | 2020 | 4.02 |
| Direct Red 80 | 3 | 1170 | 5.80 |
| Direct Yellow 106 | 4 | 1890 | 3.33 |
| Direct Yellow 106 | 5 | 1670 | 4.41 |
| Direct Yellow 106 | 6 | 464 | 7.00 |
| Acid Yellow 151 | 7 | 126 | 2.97 |
| Acid Yellow 151 | 8 | 352 | 4.08 |
| Acid Yellow 151 | 9 | 0 | 4.82 |
| Acid Black 194 | 10 | 1550 | 2.86 |
| Acid Black 194 | 11 | 1150 | 4.08 |
| Acid Black 194 | 12 | 720 | 5.18 |
| Reactive Black 5 | 13 | 363 | 3.59 |
| Reactive Black 5 | 14 | 245 | 5.00 |
| Reactive Black 5 | 15 | 79 | 6.60 |
| Reactive Red 120 | 16 | 1320 | 2.70 |
| Reactive Red 120 | 17 | 892 | 3.44 |
| Reactive Red 120 | 18 | 483 | 5.01 |

The data reveals that as the pH of the dye solution approaches 3, the ability of the alumina acetate salt fibers to adsorb dye increases significantly.

EXAMPLE 14

The ability of the alumina acetate monohydrate sol fibers to adsorb dye in different concentrations of sodium chloride (NaCl) was assessed. Previous experimentation revealed that adsorption occurs favorably at a more acidic pH, therefore the dye solutions were adjusted with concentrated hydrochloric acid (HCl). Some of the dyes precipitate salt at higher concentrations of NaCl, therefore, these dyes were tested at lower concentrations.

Dye solutions were prepared for each of the six dyes tested, the final concentration of the dye being 100 mg/L. The pH of each was adjusted with HCl. Alumina acetate monohydrate sol fibers which had been diluted 60 times and 0.1% polyacrylamide (PAA) were added, the solution then centrifuged and analyzed via visible spectroscopy for a determination of adsorption.

TABLE 9

| RUN NUMBER | C.I. NAME | ADSORPTION (mg/g) | % NaCl | pH |
|---|---|---|---|---|
| 1 | Direct Red 80 | 2080 | 0 | 3.01 |
| 2 | Direct Red 80 | 2230 | 2 | 2.98 |
| 3 | Direct Red 80 | 2670 | 5 | 2.76 |
| 4 | Direct Red 80 | 2890 | 10 | 2.63 |
| 5 | Direct Yellow 106 | 1890 | 0 | 3.33 |
| 6 | Direct Yellow 106 | 2180 | 1 | 3.06 |
| 7 | Direct Yellow 106 | 2280 | 2 | 3.07 |
| 8 | Acid Yellow 151 | 126 | 0 | 2.97 |
| 9 | Acid Yellow 151 | 287 | 1 | 3.05 |
| 10 | Acid Yellow 151 | 326 | 2 | 2.94 |
| 11 | Acid Black 194 | 1550 | 0 | 2.86 |
| 12 | Acid Black 194 | 2250 | 2 | 2.87 |
| 13 | Acid Black 194 | 2310 | 4 | 2.84 |
| 14 | Reactive Black 5 | 363 | 0 | 3.59 |
| 15 | Reactive Black 5 | 227 | 2 | 3.19 |
| 16 | Reactive Black 5 | 135 | 5 | 3.21 |
| 17 | Reactive Black 5 | 165 | 10 | 2.82 |

TABLE 9-continued

| RUN NUMBER | C.I. NAME | ADSORPTION (mg/g) | % NaCl | pH |
|---|---|---|---|---|
| 18 | Reactive Red 120 | 1320 | 0 | 2.70 |
| 19 | Reactive Red 120 | 2210 | 2 | 3.24 |
| 20 | Reactive Red 120 | 2380 | 5 | 3.05 |
| 21 | Reactive Red 120 | 2080 | 10 | 3.07 |

EXAMPLE 15

The ability of the alumina acetate monohydrate fibers to adsorb dye in different concentrations of sodium sulfate ($Na_2SO_4$) was assessed. Previous experimentation revealed that adsorption occurs favorably at a more acidic pH, therefore the dye solutions were adjusted with concentrated HCl. Some of the dyes precipitate salt at higher concentrations of $Na_2SO_4$, therfore, these dyes were tested at lower concentrations.

Dye solutions were prepared for each of the six dyes tested, the final concentration of the dye being 100 mg/L. The pH of each was adjusted with HCl. Alumina acetate monohydrate fibers which had been diluted 60 times and 0.1% PAA were added, the solution then centrifuged and analyzed via visible spectroscopy for a determination of adsorption.

TABLE 10

| RUN NUMBER | C.I. NAME | ADSORPTION (mg/g) | % $Na_2So_4$ | pH |
|---|---|---|---|---|
| 1 | Direct Red 80 | 2080 | 0 | 3.01 |
| 2 | Direct Red 80 | 1420 | 2 | 3.75 |
| 3 | Direct Red 80 | 1330 | 5 | 3.98 |
| 4 | Direct Red 80 | 785 | 10 | 4.02 |
| 5 | Direct Yellow 106 | 1890 | 0 | 3.33 |
| 6 | Direct Yellow 106 | 1120 | 1 | 3.80 |
| 7 | Direct Yellow 106 | 1140 | 2 | 3.63 |
| 8 | Acid Yellow 151 | 126 | 0 | 2.97 |
| 9 | Acid Yellow 151 | 36 | 1 | 3.62 |
| 10 | Acid Yellow 151 | 56 | 2 | 3.63 |
| 11 | Acid Black 194 | 1550 | 0 | 2.86 |
| 12 | Acid Black 194 | 1160 | 2 | 3.85 |
| 13 | Acid Black 194 | 1180 | 4 | 3.87 |
| 14 | Reactive Black 5 | 363 | 0 | 3.59 |
| 15 | Reactive Black 5 | 0 | 2 | 4.09 |
| 16 | Reactive Black 5 | 2 | 5 | 4.32 |
| 17 | Reactive Black 5 | 0 | 10 | 4.51 |
| 18 | Reactive Red 120 | 1320 | 0 | 2.70 |
| 19 | Reactive Red 120 | 355 | 2 | 4.15 |
| 20 | Reactive Red 120 | 254 | 5 | 4.32 |
| 21 | Reactive Red 120 | 0 | 10 | 4.49 |

The pH of each solution was measured after samples were obtained for centrifugation. It was found that the addition of the HCl to these solutions did not lower the pH of the solutions to 3, but rather to 4. Therefore, more favorable results, based on experimentation, might be were lowered to 3.

EXAMPLE 16

This Example tests the ability of alumina acetate monohydrate sol fibers to adsorb dye at temperatures of typical jet dyeing effluents of commercial dye houses.

Control dye solutions, at concentrations of 3 g/L, were prepared as normal at abient temperature. Test dye solutions were prepared at 65° C. and 85° C. and at concentrations of 3 g/L. Dye containers and the water used to dilute the dye were heated, and the alumina acetate monohydrate sol fibers were warmed to about 40° C. The solutions and sol were mixed while hot, poured into tubes, and centrifuged while hot. Capacity of the dye solutions were measured by UV-visible spectroscopy.

TABLE 11

| RUN NUMBER | C.I. NAME | TEMPERATURE, ° C. | ADSORPTION (mg/g) |
|---|---|---|---|
| 1 | Direct Red 80 | Ambient | 2714 |
| 2 | Direct Red 80 | 65° C. | 2393 |
| 3 | Direct Red 80 | 85° C. | 1995 |
| 4 | Direct Yellow 106 | Ambient | 1828 |
| 5 | Direct Yellow 106 | 65° C. | 1324 |
| 6 | Direct Yellow 106 | 85° C. | 1587 |
| 7 | Acid Yellow 151 | Ambient | 1549 |
| 8 | Acid Yellow 151 | 65° C. | 850 |
| 9 | Acid Yellow 151 | 85° C. | 669 |
| 10 | Acid Black 194 | Ambient | 1724 |
| 11 | Acid Black 194 | 65° C. | 1660 |
| 12 | Acid Black 194 | 85° C. | 1835 |
| 13 | Reactive Red 120 | Ambient | 944 |
| 14 | Reactive Red 120 | 65° C. | 0 |
| 15 | Reactive Red 120 | 85° C. | 1166 |
| 16 | Reactive Black 5 | Ambient | 778 |
| 17 | Reactive Black 5 | 65° C. | 766 |
| 18 | Reactive Black 5 | 85° C. | 371 |

EXAMPLE 17

The standard acrylic latex white liquid coating material was mixed with increasing percentages of alumina acetate monohydrate salt sol. This sol was chosen because of the gloss and yellowing reduction effects observed from previous testing. This sol was very viscous, but easy to mix in the liquid latex coating using an electric laboratory turbine type stirrer.

The liquid latex was coated on plate glass panels and allowed to dry for 48 hours. The percent gloss was measured, and the same panels were exposed to ultraviolet radiation for 48 hours. The following results were observed:

1. The percent gloss decreased significantly with the addition of sol.

2. Addition of colorless sol from 1–11 percent by weight reduced gloss and increased gloss after 11 percent.

3. From micrographs of the coating surfaces, the texture roughens with the addition of sol which decreases gloss; and the texture of UV exposed surfaces does not appear differently than nonexposed surfaces.

The sol was an excellent additive to latex coatings for adjusting the percent gloss. The mechanism of this phenomenon is as follows:

1. The very hydrophilic and colorless sol was added to a water borne acrylic latex liquid coating which was easily dispersed due to the amount of water present.

2. When the liquid coating was applied to a substrate, the water evaporated from the coating and the sol, which became incompatible in the absence of water.

3. The alumina acetate monohydrate particles formed nondispersed microparticles which roughen the surface slightly without an effect on color and disperse light when the gloss is measured.

The addition of pigments of selective fineness of grind (particle size) is the standard method of adjusting gloss. This sol is colorless and non-interactive, and has an excellent application as a convenient coatings additive.

EXAMPLE 18

Alumina acetate monohydrate salt fibers produced in accordance with Example 5 (Run Number 6) were compared with commercial polyelectrolytes to determine their utility in wastewater treatment.

The bench scale tests comparing the alumina acetate monohydrate salt fibers to a variety of inorganic and organic cationic polyelectrolytes were run using the same basic procedure. The product presently in use was run first to establish its dosage and performance level. After the base line was established a series of tests were run using the fibers to establish the dosage range where it gave similar performance to the product presently in use. Once the dosage range for the fibers was established then a series of direct comparison tests were run. Then a final test was run and specific performance characteristics—settling rate, floc size, effluent color and turbidity, etc.—were determined.

The feed rate of liquid Poly DADMAC (20% active) is 1.0 to 1.5 mg/l depending on how many grinding circuits are in operation. At low operating rates the dosage is closer to 1.0 mg/l. This is because there is more time available for settling. At higher rates more material is needed to maintain good recycle water quality.

Graduate cylinder settling tests were run to determine the settling rates of Poly DADMAC and the alumina acetate monohydrate salt fibers. A 5 gallon sample of tailings was collected and the polymer was added to this sample. After mixing this slurry a one liter sample was taken from the 5 gallon sample and added to a one liter graduated cylinder. Time was recorded as the slurry passed the marks on the 1,000 ml graduate. These batch clarification tests were run in the field next to the clarifier. The turbidity recorded were estimates based on direct comparison with known samples.

The following summarizes the data collected using Poly DADMAC and the fibers. The dosage required for the fibers to produce results similar to Poly DADMAC was in the 400 to 500 mg/l range.

5 GALLON BATCH CLARIFICATION TESTS

| SAMPLE # | DOSAGE MG/LITER | SETTLING RATES IN SECONDS PER 1.75 INCHES | | CLARITY |
| --- | --- | --- | --- | --- |
| | | FREE SETTLING 800 ML to 600 ML | COMPACT SETTLING 500 ML to 300 ML | |
| 1. Poly DADMAC | 1.5 | 21 | 23 | GOOD |
| 2. Poly DADMAC | 1.0 | 24 | 27 | FAIR |
| 3. Alumina Acetate Monohydrate Salt Fibers | 500.0 | 20 | 24 | GOOD |
| 4. Alumina Acetate Monohydrate Salt Fibers | 400.0 | 28 | 30 | FAIR |
| 5. Alumina Acetate Monohydrate Salt Fibers | 500.0 | 22 | 25 | GOOD |
| 6. Poly DADMAC | 1.3 | 23 | 27 | GOOD |
| 7. Poly DADMAC | 1.0 | 25 | 30 | FAIR |
| 8. Alumina Acetate Monohydrate Salt Fibers | 400.0 | 33 | 60 | FAIR |
| 9. Alumina Acetate Monohydrate Salt Fibers | 500.0 | 27 | 33 | FAIR |
| 10. Alumina Acetate Monohydrate Salt Fibers | 600.0 | 23 | 26 | GOOD |

The following describes each application and the results obtained:

Iron Ore Tailings Clarification

In preparation of iron ore one starts with crude ore and removes the silica using a magnetic separation process. The ore is first ground to minus 500 mesh in a series of wet ball and rod mills and is then passed over a series of magnets. The iron oxide is concentrated on the magnets and separated from the silica. The rejects from the magnetic separators still contain some iron ore and this is recovered in a high rate classifier. The heavier iron ore settles and the lighter silica does not settle and flows out of the system.

The rejects leave the high rate classifiers and are clarified using Poly DADMAC in large diameter clarifiers. The solids in this tailings stream vary from 3% to 5%. These units produce a recycled water quality of 100+/−20 turbidity units.

Wastewater Treatment

For several years municipalities have used high dosages (30 to 40 mg/l) of Poly Amines to remove color from textile plant wastewater. The Poly Amine (50% active) is CPS material.

Conventional jar tests were run to determine the performance of the fibers compared to Poly Amine and Poly Aluminum Chloride (70% and 83% basic). Initial color results were done by comparing one effluent sample to another. In the final series actual colors were run using a color determination procedure which involved triple filtering each sample, running each sample at three different wave lengths and using a computer to calculate the final color. The untreated colors run 600 to 800 where the secondary effluent colors run between 375 and 425. The following summarizes the results of the tests.

WASTEWATER TREATMENT PLANT
ONE LITER BATCH CLARIFICATION TESTS

| SAMPLE # | DOSAGE MG/LITER | SETTLING RATE TO 500 ML MARK | SLUDGE VOLUME AFTER 15 MINUTES | CLARITY VISUAL | CLARITY INSTRUMENT |
|---|---|---|---|---|---|
| 1. Poly Amine | 20 | 150 sec. | 200 ml | 400 | NR |
| 2. Poly Amine | 30 | 135 sec. | 200 ml | 300 | NR |
| 3. Alumina Acetate Monohydrate Salt Fibers | 500 | 180 sec. | 220 ml | 350 | NR |
| 4. Alumina Acetate Monohydrate Salt Fibers | 1,000 | 240 sec. | 240 ml | 300 | NR |
| 5. PAC 70% Basic 23% $Al_2O_3$ | 50 | 180 sec. | 200 ml | 450 | NR |
| 6. Poly Amine & PAC 70% Basic | 15 20 | 180 sec. | 200 ml | 250 | NR |
| 7. Poly Amine & Alumina Acetate Monohydrate Salt Fibers | 15 150 | 200 sec. | 220 ml | 300 | NR |
| 8. Poly Amine & Alumina Acetate Monohydrate Salt Fibers | 20 100 | 170 sec. | 210 ml | 300 | NR |
| 9. Poly Amine | 20 | 135 sec. | 200 ml | 400 | 395 |
| 10. Poly Amine | 30 | 125 sec. | 200 ml | 300 | 389 |
| 11. Poly Amine & PAC 70% Basic | 20 20 | 190 sec. | 210 ml | 200 | 394 |
| 12. Poly Amine & Alumina Acetate Monohydrate Salt Fibers | 15 150 | 180 sec. | 220 ml | 300 | 385 |
| 13. Alumina Acetate Monohydrate Salt Fibers | 300 | 160 sec. | 210 ml | 400 | 419 |
| 14. Alumina Acetate Monohydrate Salt Fibers | 600 | 180 sec. | 220 ml | 300 | 399 |

The alumina acetate monohydrate salt fibers give comparable results to the Poly Amine at 600 mg/l. The sludge volume was slightly higher and the solids settle slightly slower than the Poly Amine. The fibers have a large floc like the Poly Amine whereas the PAC has a very fine floc. The fibers measureably outperform the PAC type products.

The best results were for a combined treatment of Poly Amine (15 to 20 mg/l) and alumina acetate fibers (100 to 150 mg/l). This treatment was run several times and gave excellent results. This is important where a plant is having a toxicity problem and the Poly Amine is the cause.

Municipal Drinking Water Treatment

Municipalities clarify river water using either Alum or Poly Aluminum Chloro Sulfate (PACS) and switch back and forth from alum to PACS depending on the water quality. The alum is 17% $Al_2O_3$ and the PACS is a 50% basic product containing 10.5% $Al_2O_3$. When the alkalinity is low and the turbidity is high they use PACS. When the alkalinity is high and there is high color in the water they use alum.

All tests were run in a constant temperature bath. Untreated river water had turbidities in the 15 to 20 unit range. The water used as a comparison produced filtered water turbidities of 0.17 units. The following summarizes the results obtained. "Floc Formation" is the time in seconds it takes to see a visual pinpoint floc. "Floc Size" is a relative number with the higher numbers designating finer floc with pinpoint floc being a "12.""Clarity" is a relative measure of the clarity of the water with "1 " being distilled water and untreated water being "12".

ONE LITER BATCH CLARIFICATION TESTS

| SAMPLE | DOSAGE MG/LITER | FLOC FORMATION | FLOC SIZE | CLARITY | TURBIDITY UNFILTERED | TURBIDITY FILTERED | pH |
|---|---|---|---|---|---|---|---|
| 1. Alum | 30 | 180 sec. | 7 | 3 | 14.7 | 5.1 | 6.7 |
| 2. Alum | 40 | 120 sec. | 7 | 2 | 16.4 | 1.7 | 6.6 |
| 3. Alum | 50 | 60 sec. | 8 | 1 | 2.2 | 0.2 | 6.5 |
| 4. PACS | 30 | 120 sec. | 6 | 2 | 14.1 | 2.0 | 6.7 |
| 5. PACS | 45 | 80 sec. | 5 | 2 | 1.6 | 0.3 | 6.7 |
| 6. PACS | 60 | 45 sec. | 4 | 1 | 0.6 | 0.1 | 6.6 |

-continued

ONE LITER BATCH CLARIFICATION TESTS

| SAMPLE | DOSAGE MG/LITER | FLOC FORMATION | FLOC SIZE | CLARITY | TURBIDITY UNFILTERED | TURBIDITY FILTERED | pH |
|---|---|---|---|---|---|---|---|
| 7. Alumina Acetate Monohydrate Salt Fibers | 100 | 150 sec. | 7 | 5 | 7.5 | 5.0 | 7.0 |
| 8. Alumina Acetate Monohydrate Salt Fibers | 150 | 60 sec. | 5 | 4 | 6.0 | 4.0 | 7.0 |
| 9. Alumina Acetate Monohydrate Salt Fibers | 200 | 150 sec. | 7 | 3 | 5.0 | 1.5 | 6.8 |
| 10. Alumina Acetate Monohydrate Salt Fibers | 300 | 180 sec. | 9 | 2 | 4.2 | 1.0 | 6.7 |
| 11. Alumina Acetate Monohydrate Salt Fibers | 600 | 240 sec. | 12 | 1 | 1.8 | 0.5 | 6.2 |
| 12. Alumina Acetate Monohydrate Salt Fibers | 900 | 240 sec. | 12 | 1 | 2.4 | 0.1 | 5.2 |

The following summarizes the fiber dosages required for good flocculation (DS ONE) and color and turbidity removal (DS TWO) for each application.

| APPLICATION | PRESENT PRODUCT AND DOSAGE | ALUMINA ACETATE MONOHYDRATE SALT FIBER DS ONE | ALUMINA ACETATE MONOHYDRATE SALT FIBER DS TWO |
|---|---|---|---|
| Iron Ore Tailings | Poly DADMAC (20%) 1.0–1.5 mg/l | 400–500 mg/l | 400–500 mg/l |
| Wastewater Treatment | Poly Amine (50%) 25–35 mg/l | 100–150 mg/l | 450–600 mg/l |
| Municipal Drinking Water Treatment | Poly Aluminum Chloro Sulfate (10.5% $Al_2O_3$) 30–45 mg/l | 125–175 mg/l | 400–600 mg/l |

The alumina acetate monohydrate salt fibers worked in all three applications. It performed more like an organic polyelectrolyte (Poly DADMAC and Poly Amines) than inorganic products (alum, PAC and Poly Aluminum Chloro Sulfate). The fibers have excellent floc forming characteristics, forming a good floc at lower dosages, but requires higher dosages to obtain color and turbidity removal.

EXAMPLE 19

Sample Prepared at 130° C./0 hrs.

A 1.0 percent sol was prepared by charging a slurry comprised of 47.7 grams of basic aluminum acetate and 1452.3 grams of deionized water to a Parr reactor. The reactor was heated to 130° C. and immediately cooled to 50° C. three consecutive times. The resulting sol was discharged and a sample air dried for elemental analysis. The results were: 17.21 percent carbon, 5.43 percent hydrogen, 17.82 percent aluminum and 59.54 percent oxygen by difference. Assuming all the carbon was present as acetate ion, the acetate content was calculated to be 42.34 percent. The percent carbon, hydrogen and oxygen in this acetate was:

| ELEMENT | WEIGHT PERCENT |
|---|---|
| Carbon | 17.21 |
| Hydrogen | 2.17 |
| Oxygen | 22.95 |
| Acetate | 42.34 |

The remaining percent hydrogen, oxygen and aluminum are listed below, along with the moles, normalized moles and charge balance for these elements and the above acetate:

| ELEMENT/ION | WEIGHT PERCENT | MOLES | NORMALIZED MOLES | CHARGE BALANCE |
|---|---|---|---|---|
| Acetate | 42.34 | 0.72 | 1.09 | −1.09 |
| Aluminum | 17.82 | 0.66 | 1.00 | +3.00 |
| Hydrogen | 3.26 | 3.23 | 4.89 | +4.89 |
| Oxygen | 36.58 | 2.29 | 3.47 | −6.94 |

The charge agreement is relatively good (+7.89 versus −8.03). Assuming that two aluminum atoms exist in the compound, the empirical formula can be written as:

$$Al_2O_{2.04}(CH_3COO)_{2.18}4.90H_2O$$

What is claimed is:

1. A cationic fibrous acetate salt of boehmite alumina produced by providing a slurry of water and basic aluminum acetate, stirring the slurry to ensure substantially complete mixing thereof, reacting the slurry in a vessel at a temperature of from about 100° C. to less than 140° C. for a time and at a stirring rate sufficient to produce a fibrous cationic acetate salt of boehmite alumina having a zeta potential of greater than about 25, a weight ratio of aluminum to acetate of less than about 4, and an acetate content of from more than about 13 to about 45 weight percent.

2. The fibrous acetate of claim 1 having at least about 40% more active/reactive sites than commercial colloidal alumina.

3. The fibrous acetate of claim 1 having a surface area to total volume ratio of at least about 50%.

4. The fibrous acetate of claim 1 wherein the slurry contains on the basis of $Al_2O_3$ from about 0.5 weight % to about 30 weight % $Al_2O_3$.

5. The fibrous acetate of claim 1 wherein the slurry is stirred for from less than about 1 minute to about 60 minutes prior to initiating the reaction.

6. The fibrous acetate of claim 1 wherein the slurry is reacted at a temperature of from about 100° C. to about 130° C.

7. The fibrous acetate of claim 6 wherein the slurry is reacted at a temperature of from about 120° C. to about 130° C.

8. The fibrous acetate of claim 1 wherein the slurry is reacted for a time of from less than about 1 second to about 240 minutes.

9. The fibrous acetate of claim 8 wherein the slurry is reacted at a temperature of about 130° C. for about 120 minutes.

10. The fibrous acetate of claim 8 wherein the slurry is reacted at a temperature of about 135° C. for less than about 5 seconds.

11. The fibrous acetate of claim 10 wherein the slurry temperature increase is halted and cooling is started when the slurry temperature reaches about 135° C.

12. The fibrous acetate of claim 1 wherein the slurry is stirred during the reaction at a rate of from about 50 to about 800 rpm.

13. The fibrous acetate of claim 1 wherein the reacted slurry is cooled to a temperature of from about 20° C. to about 100° C. after completion of the reaction.

14. The fibrous acetate of claim 1 wherein the acetate content is from about 20 to about 40 weight percent.

15. A process for dyeing fibers with a dye selected from the group consisting of direct, reactive, sulfur and acid dyes whereby in the dye process undyed fibers are passed through a dye bath, containing dye which is associated with or attached to a cationic fibrous acetate salt of boehmite alumina, where the fibers to be dyed remove the dye from the fibrous acetate salt of boehmite alumina upon contact therewith;

wherein the cationic fibrous acetate salt of boehmite alumina has been formed by providing a slurry of water and basic aluminum acetate, stirring the slurry to ensure substantially complete mixing thereof, and reacting the slurry in a vessel at a temperature of from about 100° C. to less than 140° C. for a time and at a stirring rate sufficient to produce a cationic fibrous acetate salt of boehmite alumina having a zeta potential of greater than about 25, a weight ratio of aluminum to acetate of less than about 4, and an acetate content of from more than about 13 to about 45 weight percent.

16. The process of claim 15 wherein the fibrous salt has an acetate content of from about 20 to about 40 weight percent.

17. A process of treating a dye waste stream comprising the steps of (a) introducing into the stream at least one agent which forms a flocculant or precipitant with the dye, said agent consisting of a cationic fibrous acetate salt of boehmite alumina, the balance being predominantly a component selected from the group which consists of inorganic salts, coagulants, organic flocculants, polymeric flocculants, and combinations thereof, said agent being formed by providing a slurry of water and basic aluminum acetate, stirring the slurry to ensure substantially complete mixing thereof, and reacting the slurry in a vessel at a temperature of from about 100° C. to less than 140° C. for a time and at a stirring rate sufficient to produce a cationic fibrous acetate salt of boehmite alumina having a zeta potential of greater than about 25, a weight ratio of aluminum to acetate of less than about 4, and an acetate content of from more than about 13 to about 45 weight percent;

(b) forming a precipitate or flocculant of the dye and agent; and (c) separating said resulting flocculant or precipitant from the stream.

18. The process of claim 17 wherein said agent has an ionic charge opposite that of the dye contained in the dye waste stream whereby the dye is attached to the agent by ionic substitution.

19. The process of claim 18 wherein the agent has a positive ionic charge and the dye has a negative ionic charge.

20. The process of claim 19 including the step of adjusting the pH of the waste stream containing the fibrous acetate agent to between about 2 and about 8.

21. The process of claim 17 including the step of separating the dye from the precipitate or flocculant.

22. The process of claim 21 including the step of regenerating the dye from the precipitate or flocculant.

23. The process of claim 22 wherein the dye is regenerated by contacting the precipitate or flocculant with a negatively charged group.

24. The process of claim 23 wherein the negatively charged group is selected from $OH^-$ and $CO_3^{-2}$.

25. A process for removing contaminants from a municipal waste treatment stream which comprises:

a. adding a cationic fibrous acetate salt of boehmite alumina to the waste stream;

b. forming a precipitate or flocculant of the contaminants and the fibrous acetate salt; and c. separating the precipitate or flocculant from the waste stream;

wherein the cationic fibrous acetate salt of boehmite alumina has been formed by providing a slurry of water and basic aluminum acetate, stirring the slurry to ensure substantially complete mixing thereof, and reacting the slurry in a vessel at a temperature of from about 100° C. to less than 140° C. for a time and at a stirring rate sufficient to produce a cationic fibrous acetate salt of boehmite alumina having a zeta potential of greater than about 25, a weight ratio of aluminum to acetate of less than about 4, and an acetate content of from more than about 13 to about 45 weight percent.

26. The process of claim 25 including the step of adjusting the pH of the waste stream containing the fibrous acetate to between about 2 and about 8.

27. The process of claim 25 including the step of separating the contaminant from the precipitate or flocculant.

28. The process of claim 27 wherein the fibrous acetate has an ionic charge opposite that of the contaminant contained in the waste stream whereby the contaminant is attached to the fiber by ionic substitution.

29. The process of claim 28 wherein the fibrous acetate has a positive ionic charge and the contaminant has a negative ionic charge.

30. A cationic fibrous acetate salt of boehmite alumina produced by providing a slurry of water and basic aluminum acetate containing, on the basis of $Al_2O_3$, from about 0.5% to about 30% by weight $Al_2O_3$; stirring the slurry for from about 1 minute to about 60 minutes so that a substantially complete mixture is obtained; reacting the slurry in a vessel at a temperature of from about 100° C. to less than 140° C. for a time of from about 1 second to about 240 minutes and at a stirring rate sufficient to produce a fibrous cationic acetate salt of boehmite alumina having a zeta potential of greater than about 25, a weight ratio of aluminum to acetate of less than about 4, and an acetate content of from about 20 to about 40 weight percent.

31. The fibrous acetate of claim 30 wherein the slurry is reacted at a temperature of from about 100° C. to about 130° C.

32. The fibrous acetate of claim 30 wherein the slurry is stirred during the reaction at a rate of from about 50 to about 800 rpm.

33. The fibrous acetate of claim 30 wherein the reacted slurry is cooled to a temperature of from about 20° C. to about 100° C. after completion of the reaction.

34. The fibrous acetate of claim 30 wherein the basic aluminum acetate is obtained by reacting alumina trihydrate with acetic acid.

* * * * *